(12) United States Patent
Cirillo et al.

(10) Patent No.: US 6,333,325 B1
(45) Date of Patent: Dec. 25, 2001

(54) METHOD OF TREATING CYTOKINE MEDIATED DISEASES OR CONDITIONS

(75) Inventors: Pier F. Cirillo, Woodbury; Thomas A. Gilmore, Middlebury; Eugene R. Hickey, Danbury, all of CT (US); John R. Regan, Larchmont, NY (US); Lin-Hua Zhang, New Fairfield, CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 0 days.

(21) Appl. No.: 09/871,559

(22) Filed: May 31, 2001

Related U.S. Application Data

(63) Continuation of application No. 09/484,638, filed on Jan. 18, 2000.
(60) Provisional application No. 60/116,400, filed on Jan. 19, 1999.

(51) Int. Cl.[7] .......................... A61K 31/5377; A61P 19/10
(52) U.S. Cl. .................................. 514/236.5; 514/227.8; 514/235.8; 514/341
(58) Field of Search ............................. 514/236.5, 227.8

(56) References Cited

U.S. PATENT DOCUMENTS

| | | |
|---|---|---|
| 4,105,766 | 8/1978 | Alexander . |
| 4,435,567 | 3/1984 | Lugosi et al. . |
| 5,162,360 | 11/1992 | Creswell . |
| 5,686,455 | 11/1997 | Adams et al. . |
| 5,739,143 | 4/1998 | Adams et al. . |
| 5,777,097 | 7/1998 | Lee et al. . |
| 5,783,664 | 7/1998 | Lee et al. . |
| 5,859,041 | 1/1999 | Liverton et al. . |
| 5,869,043 | 2/1999 | McDonnell et al. . |
| 5,871,934 | 2/1999 | Lee et al. . |
| 5,916,760 | 6/1999 | Goeddel et al. . |
| 5,948,885 | 9/1999 | Stein et al. . |
| 6,242,453 | 6/2001 | Cirillo et al. . |

FOREIGN PATENT DOCUMENTS

| | | |
|---|---|---|
| 293 352 | 8/1991 | (DD) . |
| 0 272 866 | 6/1988 | (EP) . |
| 0 395 144 | 10/1990 | (EP) . |
| 0 418 071 | 3/1991 | (EP) . |
| 0692483 | 1/1996 | (EP) . |
| 0859054 | 8/1998 | (EP) . |
| 0922762 | 6/1999 | (EP) . |
| 0 955 293 | 10/1999 | (EP) . |
| 61228444 | 10/1986 | (JP) . |
| WO93/24458 | 9/1993 | (WO) . |
| WO94/18170 | 8/1994 | (WO) . |
| WO94/22866 | 10/1994 | (WO) . |
| WO96/25157 | 8/1996 | (WO) . |
| WO96/40143 | 12/1996 | (WO) . |
| WO97/16442 | 5/1997 | (WO) . |
| WO97/22704 | 6/1997 | (WO) . |
| WO97/33883 | 9/1997 | (WO) . |
| WO97/35855 | 10/1997 | (WO) . |
| WO97/35856 | 10/1997 | (WO) . |
| WO97/44467 | 11/1997 | (WO) . |
| WO97/47618 | 12/1997 | (WO) . |
| WO97/48697 | 12/1997 | (WO) . |
| WO98/07425 | 2/1998 | (WO) . |
| WO98/15618 | 4/1998 | (WO) . |
| WO98/27098 | 6/1998 | (WO) . |
| WO98/52558 | 11/1998 | (WO) . |
| WO98/52559 | 11/1998 | (WO) . |
| WO99/00357 | 1/1999 | (WO) . |
| WO99/32106 | 7/1999 | (WO) . |
| WO99/32110 | 7/1999 | (WO) . |
| WO99/32111 | 7/1999 | (WO) . |
| WO99/32455 | 7/1999 | (WO) . |
| WO99/32463 | 7/1999 | (WO) . |
| WO99/46244 | 9/1999 | (WO) . |

OTHER PUBLICATIONS

International Search Rept. Boehrigner Ingelheim Pharmaceut. Inc. Apr. 12, 2000.

Jeffrey C. Boehm & Jerry L. Adams, New inhibitors of p38 kinase, Expert Opin.Ther. Patents (2000) 10(1):25–37.

Two novel structural classes of P38 kinase inhibitors; Exp. Opin. Ther. Patents (1999) 9(4) 477–480.

SB 203580, Calbiochem—Cat. No. 559389—Revised May 30, 1997.

Jagadish C. Sircar, et al; Pyrazolo[5,1–b] quinazolin–9 ones: A New Series of Antiallergic Agents, J. Med. Chem. 1981, 24, 735–742.

Application No. 09/611,109 filed Jun. 7, 2000; Zhang, L. et al; Process for Synthesis of Heteroaryl Substituted Urea Compounds Useful as Antiinflammatory Agents.

*Primary Examiner*—Robert W. Ramsuer
(74) *Attorney, Agent, or Firm*—Robert P. Raymond; Anthony P. Bottino; Alan R. Stempel

(57) ABSTRACT

Disclosed are novel aromatic heterocyclic compounds of the formula(I) wherein $Ar_1, Ar_2, L, Q$ and $X$ are described herein. The compounds are useful in pharmaceutic compositions for treating diseases or pathological conditions involving inflammation such as chronic inflammatory diseases. Also disclosed are processes of making such compounds.

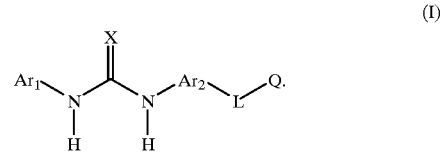

(I)

6 Claims, No Drawings

METHOD OF TREATING CYTOKINE MEDIATED DISEASES OR CONDITIONS

APPLICATION DATA

This application is a continuation of U.S. application Ser. No. 09/484,638 filed Jan. 18, 2000 which claim benefit to provisional application 60/116,400 filed Jan. 19, 1999.

TECHNICAL FIELD OF THE INVENTION

This invention relates to methods of treating certain cytokine mediated diseases or conditions using novel aromatic heterocyclic compounds of the formula(I) wherein $Ar_1$, $Ar_2$, L, Q and X are described herein:

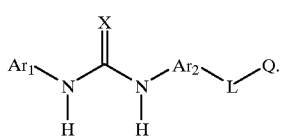

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A. et al., 1984, Rev. Infect. Disease 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, J. Invest. Med. 43: 28–38). An important and accepted therapeutic approach for potential drug intervention in these diseases is the reduction of proinflammatory cytokines such as TNF (also referred to in its secreted cell-free form termed TNFα) and IL-1β. A number of anti-cytokine therapies are currently in clinical trials. Efficacy has been demonstrated with monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., April 24–5, 1997). These include the treatment of rheumatoid arthritis, Crohn's disease and ulcerative colitis (Rankin E. C. C., et al., 1997, British J. Rheum. 35: 334–342 and Stack, W. A., et al. 1997, Lancet 349: 521–524). The monoclonal antibody is thought to function by binding to both soluble TNFα and to membrane bound TNF.

A soluble TNFα receptor has been engineered that interacts with TNFα. The approach is similar to that described above for monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, Nature Biotechnology 15: 1240). Another version of the TNFα receptor, Ro 45–2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, Inflamm. Res. 46: S143). IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, Nutrution 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, Biomed Pharmacother. 51, 58). Nitric oxide (NO) is a mediator of cardiovascular homeostatis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, J Bone Miner Res. 11, 300). The promotion of beta-cell destruction leading to insulin dependent diabetes mellitis shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, Proc Soc Exp Biol Med. 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., Proc. Natl. Acad. Sci. U.S.A., 1992, 89, 4888). Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, Ailment Pharmacol Ther. 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, Med Hypootheses 45, 559). A role for IL-1 in the pathogenic of human immunodeficiency virus (HIV) has been identified. IL-1ra showed a clear relationship to acute inflammatory events as well as to the different disease stages in the pathophysiology of HIV infection (Kreuzer, et al., 1997, Clin Exp Immunol. 109, 54). IL-1 and TNF are both involved in periodontal disease. The destructive process associated with periodontal disease may be due to a disregulation of both IL-1 and TNF (Howells, 1995, Oral Dis. 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist wash shown to inhibit fatty streak formation (Elhage et al., 1988, *Circulation,* 97, 242).

The abnormal expression of inducible nitric oxide synthetase (iNOS) has been associated with hypertension in the spontaneously hypertensive rat (Chou et al., 1998, *Hypertension,* 31, 643). IL-1 has a role in the expression of iNOS and therefore may also have a role in the pathogenesis of hypertension (Singh et al., 1996, *Amer. J. Hypertension* 9, 867).

IL-1 has also been shown to induce uveitis in rats which could be inhibited with IL-1 blockers. (Xuan et al., 1988, *J. Ocular Pharmacol. and Ther.,* 14, 31). Cytokines including IL-1, TNF and GM-CSF have been shown to stimulate proliferation of acute myelogenous luekemia blasts (Bruserud, 1996, *Leukemia Res.* 20, 65). IL-1 was shown to be essential for the development of both irritant and allergic contact dermatitis. Epicutaneous sensitization can be prevented by the administration of an anti- IL-1 monoclonal antibody before epicutaneous application of an allergen (Muller, et al., 1996, *Am J Contact Dermat.* 7, 177). Data obtain from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophilis into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hermodialysis, leukopherisis, granulocyte transfusion associated syndromes, and necrotizing entrercolitis. Rhinovirus triggers the production of various proinflammatory cytokines, predominantly IL-8, which results in symptomatic illnesses such as acute rhinitis (Winther et al., 1998, *Am J Rhinol* 12, 17).

Other diseases that are effected by IL-8 include mycardial ischemia and reperfusion, inflammtory bowel disease and many others.

The proinflammatory cytokine IL-6 has been implicated with the acute phase response. IL-6 is a growth factor in a number in oncological diseases including multiple myeloma and realted plasma cell dyscrasias (Treon, et al., 1988, *Current Opinion in Hematology* 5:42). It has also been shown to be an important mediator of inflammation within the central nervous system. Elevated levels of IL-6 are found in several neurological disorders including AIDS dememtia complex, Alzheimer's disease, multiple sclerosis, systemic lupis erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21:487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both sympton formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, Protein Sci. 6, 929). Compounds that interfered with the production of cytokines including IL-6, and TNF were effective in blocking a passive cutaneous anaphylaxis in mice (Scholz et al., 1998, *J. Med. Chem.* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1988, *Curr Opin Hematol.* 5, 22). Following kidney transplantation, a patient was diagnosed with acute myelogenous leukemia. Retrospective analysis of peripheral blood cytokines revealed elevated levels of GM-CSF and IFNγ. These elevated levels coincided with a rise in peripheral blood white cell count (Burke, et al., 1995, Leuk Lymphoma. 19, 173). The development of insulin-dependent diabetes (Type 1) can be correlated with the accumulation in pancreatic islet cells of T-cells producing IFN γ (Ablumunits, et al., 1998, *J Autoimmun.* 11, 73).

IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol,* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998 *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN 65 is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exits for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Ailment Pharmacol Ther.* 10 *Suppl* 2, 43). An elevated level of serum IgE is associated with various atopic disease such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytoline mediated diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytoline production will be beneficial in the treatment of various disease states.

It is therefore an object of the invention to provide of method of treating treating certain cytokine mediated diseases or conditions using novel aromatic heterocyclic compounds of the formula(I) wherein $Ar_1$, $Ar_2$, L, Q and X are described herein.

DETAILED DESCRIPTION OF THE INVENTION

The present invention is directed to compounds of the formula (I):

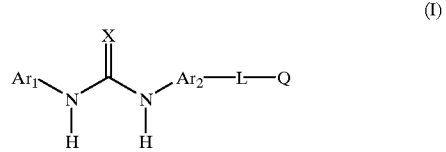

(I)

wherein $Ar_1$ is a heterocyclic group selected from the group consisting of pyrrole, pyrrolidine, pyrazole, imidazole, oxazole, thiazole, furan and thiophene; and wherein $Ar_1$ may be substituted by one or more $R_1$, $R_2$ or $R_3$;

$Ar_2$ is: phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three $R_2$ groups;

L, a linking group, is a:

$C_{1-10}$ saturated or unsaturated branched or unbranched carbon chain;

wherein one or more methylene groups are optionally independently replaced by O, N or S; and wherein said linking group is optionally substituted with 0–2 oxo groups and one or more $C_{1-4}$ branched or unbranched alkyl which may be substituted by one or more halogen atoms;

Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl) amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di($C_{1-3}$ alkyl) amino-$C_{1-3}$ alkyl, phenylamino-$C_{1-3}$ alkyl and $C_{1-3}$ alkoxy-$C_{1-3}$ alkyl;

c) $C_{1-6}$ alkoxy, secondary or tertiary amine wherein the amino nitrogen is covalently bonded to groups selected from the group consisting of $C_{1-3}$ alkyl and $C_{1-5}$ alkoxyalkyl and phenyl wherein the phenyl ring is optionally substituted with one or two groups consisting of halogen, $C_{1-6}$ alkoxy, hydroxy, or mono- or di-($C_{1-3}$ alkyl)amino, $C_{1-6}$ alkyl-S(O)$_r$, phenyl-S(O)$_r$, wherein the phenyl ring is optionally substituted with one or two groups consisting of halogen, $C_{1-6}$ alkoxy, hydroxy or mono- or di-($C_{1-3}$ alkyl)amino;

$R_1$ is selected from the group consisting of:
(a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkylkoxy which is optionally partially or fully halogenated, $NH_2C(O)$ and di($C_{1-3}$)alkylaminocarbonyl;

(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;

(c) $C_{3-10}$ branched alkenyl which may optionally be partially or fully halogenated, and which is optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkyloxy which is optionally partially or fully halogenated, $NH_2C(O)$, mono- or di($C_{1-3}$)alkylaminocarbonyl;

(d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

(e) cyano; and,
(f) methoxycarbonyl, ethoxycarbonyl and propoxycarbonyl;

$R_2$ is selected from the group consisting of:
a $C_{1-6}$ branched or unbranched alkyl which may optionally be partially or fully halogenated, acetyl, aroyl, $C_{1-4}$ branched or unbranched alkoxy, which may optionally be partially or fully halogenated, halogen, methoxycarbonyl and phenylsulfonyl;

$R_3$ is selected from the group consisting of:
a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl; wherein such phenyl, naphthyl or heterocyclic group is optionally substituted with one to five groups selected from the group consisting of a $C_{1-6}$ branched or unbranched alkyl, phenyl, naphthyl, heterocycle selected from the group hereinabove described, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which may optionally be partially or fully halogenated, phenyloxy, naphthyloxy, heteraryloxy wherein the heterocyclic moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-5}$ alkyl-C(O)-$C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$)alkylamino-S(O)$_2$, $R_4$-$C_{1-5}$ alkyl, $R_5$-$C_{1-5}$ alkoxy, $R_6$-C(O)-$C_{1-5}$ alkyl and $R_7$-$C_{1-5}$ alkyl($R_8$)N;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$) alkylamino, phenylamino, naphthylamino, heterocyclylamino wherein the heterocyclyl moiety is selected from the group hereinabove described, $NH_2C(O)$, a mono- or di-$(C_{1-3})$alkyl aminocarbonyl, $C_{1-4}$ alkyl-OC(O), $C_{1-5}$ alkyl-C(O)-$C_{1-4}$ branched or unbranched alkyl, an amino-$C_{1-5}$ aklyl, mono- or di-$(C_{1-3})$alkylamino-$C_{1-5}$ alkyl, $R_9$-$C_{1-5}$ alkyl, $R_{10}$-$C_{1-5}$ alkoxy, $R_{11}$-C(O)-$C_{1-5}$ alkyl, and $R_{12}$-$C_{1-5}$ alkyl($R_{13}$)N;

c) cycloalkyl selected from the group consisting of cyclopentanyl, cyclohexanyl, cycloheptanyl, bicyclopentanyl, bicyclohexanyl and bicycloheptanyl, which the cycloalkyl may optionally be partially or fully halogenated and which may optionally be substituted with one or three $C_{1-3}$ alkyl groups;

d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups; and e) acetyl, aroyl, alkoxycarbonylalkyl or phenylsulfonyl;

f) $C_{1-6}$ branched or unbranched alkyl which may optionally be partially or fully halogenated;

wherein or $R_1$ or $R_2$ taken together may optionally form a fused phenyl or pyridinyl ring, each $R_8$, $R_{13}$ is independently selected from the group consisting of:

hydrogen and $C_{1-4}$ branched or unbranched alkyl which may optionally be partially or fully halogenated;

each $R_4$, $R_5$, $R_6$, $R_7$, $R_9$, $R_{10}$, $R_{11}$ and $R_{12}$ is independently selected from the group consisting of:

morpholine, piperidine, piperazine, imidazole and tetrazole;

m=0, 1, 2;

r=0, 1, 2;

t=0, 1, 2;

X=O or S and physiologically acceptable acids or salts thereof.

A preferred subgeneric aspect of the invention comprises compounds of the formula(I) wherein $Ar_2$ is naphthyl, tetrahydronaphthyl, indanyl or indenyl.

A more preferred subgeneric aspect of the invention comprises compounds of the formula(I) wherein $Ar_2$ is naphthyl.

A yet more preferred subgeneric aspect of the invention comprises compounds of the formula(I), as described in the immediate previous paragraph, wherein:

$Ar_1$ is thiophene or pyrazole;

$Ar_2$ is 1-naphthyl;

L is $C_{1-6}$ saturated or unsaturated branched or unbranched carbon chain wherein one or more methylene groups are optionally independently replaced by O,N or S; and wherein said linking group is optionally substituted with 0–2 oxo groups and one or more $C_{1-4}$ branched or unbranched alkyl which may be substituted by one or more halogen atoms;

$R_1$ is selected from the group consisting of $C_{1-4}$alkyl branched or unbranched, cyclopropyl and cyclohexyl which may optionally be partially or fully halogenated and which may optionally be substituted with one to three $C_{1-3}$ alkyl groups;

$R_3$ is selected from the group consisting of $C_{1-4}$alkyl branched or unbranched, cyclopropyl, phenyl, pyridinyl each being optionally substituted as described above, alkoxycarbonylalkyl; $C_{1-6}$alkyl branched or unbranched; cyclopropyl or cyclopentyl optionally substituted as described above.

A yet further preferred subgeneric aspect of the invention comprises compounds of the formula (I), as described in the immediate previous paragraph, wherein $Ar_1$ is pyrazole.

A still yet further preferred subgeneric aspect of previous the invention comprises compounds of the formula (I), as described in the immediate paragraph, wherein L is $C_{1-5}$ saturated carbon claim wherein one or more methylene groups are optionally independently replaced by O,N or S; and wherein said linking group is optionally substituted with 0–2 oxo groups and one or more $C_{1-4}$ branched or unbranched alkyl which may be substiututed by one or more halogen atoms;

Particularly preferred embodiments of L are propoxy, ethoxy, methoxy, methyl, propyl, $C_{3-5}$ acetylene or methylamino each being optionally substituted are described herein.

A more particularly preferred embodiment of L is ethoxy optionally substituted.

The following compounds are representative of the compounds of formula(I):

1-[5-tert-Butyl-2-p-tolyl-2H-pyrazol-3-yl]-3-[4-(2-morpholin-4-yl-ethoxy)naphthalen-1-yl]urea;

1-[5-tert-Butyl-2-p-tolyl-2H-pyrazol-3-yl]-3-[4-(2-(cis-2,6-dimethylmorpholin-4-yl)ethoxy)naphthalen-1-yl]-urea;

1-[5-tert-Butyl-2-p-tolyl-2H-pyrazol-3-yl]-4-[4-(2-(trans-2,6-dimethylmorpholin-4-yl)ethoxy)naphthalen-1-yl]-urea;

1-[5-tert-Butyl-2-p-tolyl-2H-pyrazol-3-yl]-3-[4-(2-(2-(methoxymethyl)morpholin-4-yl)ethoxy)naphthalen-1-yl]-urea;

1-[5-tert-Butyl-2-p-tolyl-2H-pyrazol-3-yl]-3-[4-(2-(morpholin-4-yl)-2-oxoethoxy)naphthalen-1-yl]-urea;

1-[5-tert-Butyl-2-p-tolyl-2H-pyrazol-3-yl]-3-[4-(2-(morpholin-4-yl)-2-methylethoxy)naphthalen-1-yl]-urea;

1-[5-tert-Butyl-2-p-tolyl-2H-pyrazol-3-yl]-3-[4-(2-(morpholin-4-yl)-1-methylethoxy)naphthalen-1-yl]urea;

1-[5-tert-Butyl-2-p-tolyl-2H-pyrazol-3-yl]-3-[4-(2-thiomorpholin-4-yl-ehtoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-Butyl-2-p-tolyl-2H-pyrazol-3-yl]-3-[4-(2-morpholin-4-yl-ethoxy)-3-methylnaphthalen-1-yl]-urea;

1-[5-tert-Butyl-2-p-tolyl-2H-pyrazol-3-yl]-3-[4-(2-piperidin-4-yl-ethoxy)naphthalen-1-yl]-urea;

1-[5-tert-Butyl-2-p-tolyl-2H-pyrazol-3-yl]-3-[4-(2-(1-acetylpiperidin-4-yl)ethoxy)naphthalen-1-yl]-urea;

1-[5-tert-Butyl-2-p-tolyl-2H-pyrazol-3-yl]-3-[4-(2-thiazolidin-3-yl-ethoxy)naphthalen-1-yl]-urea;

1-[5-tert-Butyl-2-p-tolyl-2H-pyrazol-3-yl]-3-[4-(2-(morpholin-4-yl-carbonyloxo)ethoxy)naphthalen-1-yl]-urea;

1-[5-tert-Butyl-2-p-tolyl-2H-pyrazol-3-yl]-3-[4-(2-(tetrahydropyran-4-yl)ethoxy)naphthalen-1-yl]-urea;

1-[5-tert-Butyl-2-p-tolyl-2H-pyrazol-3-yl]-3-[4-(2-(N-methyl-2-methoxyethylamino)ethoxy)naphthalen-1-yl]-urea;

1-[5-tert-Butyl-2-p-tolyl-2H-pyrazol-3-yl]-3-[4-(2-(1-oxo-tetrahydrothiophen-3-yl)ethoxy)naphthalen-1-yl]-urea;

1-[5-tert-Butyl-2-p-tolyl-2H-pyrazol-3-yl]-3-[4-(3-morpholin-4-yl-propyl)naphthalen-1-yl]-urea;

1-[5-tert-Butyl-2-p-tolyl-2H-pyrazol-3-yl]-3-[4-(morpholin-4-yl-methyl)naphthalen-1-yl]-urea;

1-[5-tert-Butyl-2-p-tolyl-2H-pyrazol-3-yl]-3-[4-(3-thiazolidin-3-yl-propyl)naphthalen-1-yl]-urea;

1-[5-tert-Butyl-2-p-tolyl-2H-pyrazol-3-yl]-3-[4-(3-(tetrahydropyran-2-yl-oxy)propyl)naphthalen-1-yl]-urea;
1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(2-pyridin-4-yl-ethenyl)naphthalen-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(methoxymethyloxy)propyn-1-yl)naphthalen-1-yl]-urea;
1-[5-tert-Butyl-2-p-tolyl-2H-pyrazol-3-yl]-3-[4-(3-(morpholin-4-yl)-3-methylpropyn-1-yl)naphthalen-1-yl]-urea;
1-[5-tert-Butyl-2-p-tolyl-2H-pyrazol-3-yl]-3-[4-(3-(morpholin-4-yl)-3,3-dimethylpropyn-1-yl)naphthalen-1-yl]-urea;
1-[5-tert-Butyl-2-p-tolyl-2H-pyrazol-3-yl]-3-[4-(3-tetrahydropyran-2-yl-oxy)butyn-1-yl)naphthalen-1-yl]-urea;
1-[5-tert-Butyl-2-p-tolyl-2H-pyrazol-3-yl]-3-[4-(3-(furan-2-ylcarbonyloxy)propyn-1-yl)naphthalen-1-yl]-urea;
1-[5-tert-Butyl-2-p-tolyl-2H-pyrazol-3-yl]-3-[4-(3-(piperidin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-benzimidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)-ethoxy)naphthalen-1-yl]-urea;
1-[5-tert-Butyl-2-p-tolyl-2H-pyrazol-3-yl]-3-[4-(pyridin-4-yl-methylamino)naphthalen-1-yl]-urea;
1-[5-tert-Butyl-2-p-tolyl-2H-pyrazol-3-yl]-3-[4-(pyridin-4-yl-carbonylamino)naphthalen-1-yl]-urea;
1-[5-tert-Butyl-2-p-tolyl-2H-pyrazol-3-yl]-3-[4-(morpholin-4-yl-acetamido)naphthalen-1-yl]-urea;
1-[5-tert-Butyl-2-p-tolyl-2H-pyrazol-3-yl]-3-[4-(pyridin-3-yl-methylamino)naphthalen-1-yl]-urea;
1-[5-tert-Butyl-2-p-tolyl-2H-pyrazol-3-yl]-3-[4-(pyridin-3-yl-carbonylamino)naphthalen-1-yl]-urea;
1-[5-iso-Propyl-2-phenyl-2H-pyrazol-3-yl]-3-[4-(2-morpholine-4-yl-ethoxy)naphthalen-1-yl]-urea;
1-[5-(Tetrahydropyran-3-yl)-2-phenyl-2H-pyrazol-3-yl]-3-[4-(2-morpholin-4-yl-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl] 3-[4-(2-morpholin-4-yl-ethoxy)naphthalen-1-yl]-urea;
1-[5-ethoxycarbonyl-2-phenyl-2H-pyrazol-3-yl]-3-[4-(2-morpholin-4-yl-ethoxy)naphthalen-1-yl]-urea;
1-[5-(1-methylcyclohex-1-yl)-2-phenyl-2H-pyrazol-3-yl]-3-[4-(2-morpholin-4-yl-ethoxy)naphthalen-1-yl]-urea;
1-[5-tert-butyl-2-methyl-2H-pyrazol-3-yl]-3-[4-(2-morpholin-4-yl-ethoxy)naphthalen-1-yl]-urea;
1-[5-tert-butyl-2-benzyl-2H-pyrazol-3-yl]-3-[4-(2-morpholin-4-yl-ethoxy)naphthalen-1-yl]-urea;
1-[5-tert-butyl-2-(4-chlorophenyl)-2H-pyrazol-3-yl]-3-[4-(2-morpholin-4-yl-ethoxy)naphthalen-1-yl]-urea;
1-[5-tert-butyl-2-butyl-2H-pyrazol-3-yl]-3-[4-(2-morpholin-4-yl-ethoxy)naphthalen-1-yl]-urea;
1-[5-tert-butyl-2-(ethoxycarbonylmethyl)-2H-pyrazol-3-yl]-3-[4-(2-morpholin-4-yl-ethoxy)naphthalen-1-yl]-urea;
1-[5-tert-butyl-2-(4-methyl-3-carbamylphenyl)-2H-pyrazol-3-yl]-3-[4-(2-morpholin-4-yl-ethoxy)naphthalen-1-yl]-urea;
1-[5-tert-butyl-2-(4-methyl-3-(2-ethoxycarbonylvinyl)phenyl)-2H-pyrazol-3-yl]-3-[4-(2-morpholin-4-yl-ethoxy)naphthalen-1-yl]-urea;
1-[5-tert-butyl-2-(4-methyl-3-(morpholin)-4-yl)methylphenyl)-2H-pyrazol-3-yl]-3-[4-(2-morpholin-4-yl-ethoxy)naphthalen-1-yl]-urea;
1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;
1-[5-tert-butyl-2-(3-(2-morpholin-4-yl-ethyl)phenyl)-2H-pyrazol-3-yl]-3-[4-(2-morpholin-4-yl-ethoxy)naphthalen-1-yl]-urea;
1-[5-tert-butyl-2-(3-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(3-dimethylaminomethylphenyl)-2H-pyrazol-3-yl]-3-[4-(2-morpholin-4-yl-ethoxy)naphthalen-1-yl]-urea;
1-[5-tert-butyl-2-(4-(tetrahydropyran-4-ylamino)-phenyl)-2H-pyrazol-3-yl]-3-[4-(2-morpholin-4-yl-ethoxy)naphthalen-1yl]-urea;
1-[5-tert-butyl-2-(4-(3-benzylureido)phenyl)-2H-pyrazol-3-yl]-3-[4-(2-morpholin-4-yl-ethoxy)naphthalen-1-yl]-urea;
1-[5-tert-butyl-2-(2-chloropyridin-5-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-morpholin-4-yl-ethoxy)naphthalen-1-yl]-urea;
1-[5-tert-butyl-2-(2-methoxypyridin-5-yl)-2H-pyrazol-3-yl]-3-[4-(2-morpholin-4-yl-ethoxy)naphthalen-1-yl]-urea;
1-[5-tert-butyl-2-(pyridin-3-yl)-2H-pyrazol-3-yl]-3-[4-(2morpholin-4-yl-ethoxy)naphthalen-1-yl]-urea;
1-[5-tert-butyl-2-(2-methylpyridin-5-yl)-2H-pyrazol-3-yl]-3-[4-(2-pyridin-4-yl-ethoxy)naphthalen-1-yl]-urea;
1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;
1-[5-tert-butyl-2-(2-methylpyridin-5-yl)-2H-pyrazol-3-yl]-3-[4-(3-morpholin-4-yl-propyn-1-yl)naphthalen-1-yl]-urea;
1-[5-tert-Butyl-2-p-tolyl-2H-pyrazol-3-yl]-3-[4-(2-(2-dimethylaminomethylmorpholin-4-yl)ethoxy)naphthalen-1-yl]-urea;
1-[5-tert-butyl-2-iso-propyl-2H-pyrazol-3-yl]-3-[4-(2-morpholin-4-yl-ethoxy)naphthalen-1-yl]-urea;
1-[5-tert-butyl-2-cyclopropyl-2H-pyrazol-3-yl]-3-[4-(2-morpholin-4-yl-ethoxy)naphthalen-1-yl]-urea;
1-[5-tert-butyl-2-(thiophen-3-yl)-2H-pyrazol-3-yl]-3-[4-(2-morpholin-4-yl-ethoxy)naphthalen-1-yl]-urea;
1-[5-tert-butyl-2-cyclopentyl-2H-pyrazol-3-yl]-3-[4-(2-morpholin-4-yl-ethoxy)naphthalen-1-yl]-urea;
1-[5-tert-butyl-2-iso-propyl-2H-pyrazol-3-yl]-3-[4-(tetrahydropyran-4-yl-ethoxy)naphthalen-1-yl]-urea;
1-[5-tert-butyl-2-cyclopropyl-2H-pyrazol-3-yl]-3-[4-(1-oxo-tetrahydrothiophen-3-yl-ethoxy)naphthalen-1-yl]-urea;

1-[5-tert-butyl-2-(thiophen-3-yl)-2H-pyrazol-3-yl]-3-[4-(2-pyridinyl-4-yl-ethoxy)naphthalen-1-yl]-urea;
1-[5-tert-butyl-2-cyclopentyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(3-(pyridin-4-yl)propyn-1yl)naphthalen-1-yl]-urea;
1-[5-tert-Butyl-2-p-tolyl-2H-pyrazol-3-yl]-3-[4-(3-(2-methylaminopyridin-4-yl)propyn-1-yl)naphthalen-1-yl]-urea;
1-[5-tert-Butyl-2-p-tolyl-2H-pyrazol-3-yl]-3-[4-(3-(1-oxo-tetrahydothiophen-3-yl)propyn-1-yl)naphthalen-1-yl]-urea;
1-[5-tert-Butyl-2-p-tolyl-2H-pyrazol-3-yl]-3-[4-(3-(thiazolidin-3-yl)propyn-1-yl)naphthalen-1-yl]-urea;
1-[5-tert-Butyl-2-p-tolyl-2H-pyrazol-3-yl]-3-[4-(3-(tetrahydropyran-4-yl)propyn-1-yl)naphthalen-1-yl]-urea;
1-[5-tert-Butyl-2-p-tolyl-2H-pyrazol-3-yl]-3-[4-(2-methylaminopyrimidin-4-yl-methoxy)naphthalen-1-yl]-urea;
1-[5-tert-Butyl-2-p-tolyl-2H-pyrazol-3-yl]-3-[4-(2-(2-methylaminopyrimidin-4-yl)ethoxy)naphthalen-1-yl]-urea;
1-[5-tert-Butyl-2-p-tolyl-2H-pyrazol-3-yl]-3-[4-(2-(4-methoxybenzimidazol-1-yl)ethoxy)naphthalen-1-yl]-urea;
1-[5-tert-Butyl-2-p-tolyl-2H-pyrazol-3-yl]-3-[4-(2-(4-methylaminobenzimidazol-1-yl)ethoxy)naphthalen-1-yl]-urea;
1-[5-tert-Butyl-2-p-tolyl-2H-pyrazol-3-yl]-3-[4-(2-(2-imidazo[4,5-b]pyridin-1yl)ethoxy)naphthalen-1-yl]-urea;
1-[5-tert-Butyl-2-p-tolyl-2H-pyrazol-3-yl]-3-[4-(2-[1,8]naphthyridin-4-yl)ethoxy) naphthalen-1-yl]-urea;
1-[5-tert-Butyl-2-p-tolyl-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-pyridin-3-yl-2H-pyrazol-3-yl]-3-[4-(2-methylaminopyrimidin-4-yl-methoxy)naphthalen-1-yl]-urea;
1-[5-tert-Butyl-2-(2-methylpyridin-5-yl) -2H-pyrazol-3-yl]-3-[4-(2-(2-methylaminopyrimidin-4-yl)ethoxy)naphthalen-1-yl]-urea;
1-[5-tert-Butyl-2-(2-methylpyridin-5-yl)-2H-pyrazol-3-yl]-3-[4-(2-(4-methoxybenzimidazol-1-yl)ethoxy)naphthalen-1-yl]-urea;
1-[5-tert-Butyl-2-(2-methylpyridin-5-yl)-2H-pyrazol-3-yl]-3-[4-(2-(4-methylaminobenzimidazol-1-yl)ethoxy)naphthalen-1-yl]-urea;
1-[5-tert-Butyl-2-(2-methylpyridin-5-yl)-2H-pyrazol-3-yl]-3-[4-(2-(2-imidazo[4,5-b]pyridin-1-yl)ethoxy)naphthalen-1-yl]-urea;
1-[5-tert-Butyl-2-(2-methylpyridin-5-yl)-2H-pyrazol-3-yl]-3-[4-(2-[1,8]naphthyridin-4-yl)ethoxy)naphthalen-1-yl]-urea;
1-[5-tert-Butyl-2-(2-methylpyridin-5-yl)-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-cyclopropyl-2H-pyrazol-3-yl]-3-[4-(2-methylaminopyrimidin-4-yl-methoxy)naphthalen-1-yl]-urea;
1-[5-tert-Butyl-2-cyclopropyl-2H-pyrazol-3-yl]-3-[4-(2-(2-methylaminopyrimidin-4-yl)ethoxy)naphthalen-1-yl]-urea;
1-[5-tert-Butyl-2-cyclopropyl-2H-pyrazol-3-yl]-3-[4-(2-(4-methoxybenzimidazol-1-yl)ethoxy)naphthalen-1-yl]-urea;
1-[5-tert-Butyl-2-cyclopropyl-2H-pyrazol-3-yl]-3-[4-(2-(4-methylaminobenzimidazol-1-yl)ethoxy)naphthalen-1-yl]-urea;
1-[5-tert-Butyl-2-methyl-2H-pyrazol-3-yl]-3-[4-(2-(2-imidazo[4,5-b]pyridin-1-yl)ethoxy)naphthalen-1-yl]-urea;
1-[5-tert-Butyl-2-methyl-2H-pyrazol-3-yl]-3-[4-(2-[1,8]naphthyridin-4-yl)ethoxy)naphthalen-1-yl]-urea;
1-[5-tert-Butyl-2-methyl-2H-pyrazol-3-yl]-3-[4-(2-(3,4-dihydro-2H-pyrano[2,3-b]pyridin-5-yl)ethoxy)naphthalen-1-yl]-urea
and their physiologically acceptable acids or salts thereof.

Preferred compounds of the formula(I) are:
1-[5-tert-Butyl-2-p-tolyl-2H-pyrazol-3-yl]-3-[4-(2-morpholin-4-yl-ethoxy)naphthalen-1-yl]-urea;
1-[5-tert-Butyl-2-p-tolyl-2H-pyrazol-3-yl]-3-[4-(2-(cis-2,6-dimethylmorpholin-4-yl)ethoxy)naphthalen-1-yl]-urea;
1-[5-tert-Butyl-2-p-tolyl-2H-pyrazol-3-yl]-3-[4-(2-(trans-2,6-dimethylmorpholin-4-yl)ethoxy)naphthalen-1-yl]-urea;
1-[5-tert-Butyl-2-p-tolyl-2H-pyrazol-3-yl]-3-[4-(2-(2-(methoxymethyl)morpholin-4-yl)ethoxy)naphthalen-1-yl]-urea;
1-[5-tert-Butyl-2-p-tolyl-2H-pyrazol-3-yl]-3-[4-(2-(morpholin-4-yl)-2-oxoethoxy)naphthalen-1-yl]-urea;
1-[5-tert-Butyl-2-p-tolyl-2H-pyrazol-3-yl]-3-[4-(2-(morpholin-4-yl)-2-methyl-ethoxy)naphthalen-1-yl]-urea;
1-[5-tert-Butyl-2-p-tolyl-2H-pyrazol-3-yl]-3-[4-(2-(morpholin-4-yl)-1-methyl-ethoxy)naphthalen- I -yl]-urea;
1-[5-tert-Butyl-2-p-tolyl-2H-pyrazol-3-yl]-3-[4-(2-thiomorpholin-4-yl-ethoxy)naphthalen-1-yl]-urea;
1-[5-tert-Butyl-2-p-tolyl-2H-pyrazol-3-yl]-3-[4-(2-(1-oxothiomorpholin-4-yl)ethoxy)naphthalen-1-yl]-urea;
1-[5-tert-Butyl-2-p-tolyl-2H-pyrazol-3-yl]-3-[4-(2-morpholin-4-yl-ethoxy)-3-methylnaphthalen-1-yl]-urea;
1-[5-tert-Butyl-2-p-tolyl-2H-pyrazol-3-yl]-3-[4-(2-(morpholin-4-yl-carbonyloxo)ethoxy)naphthalen-1-yl]-urea;
1-[5-tert-Butyl-2-p-tolyl-2H-pyrazol-3-yl]-3-[4-(2-(tetrahydropyran-4-yl)ethoxy)naphthalen-1-yl]-urea;
1-[5-tert-Butyl-2-p-tolyl-2H-pyrazol-3-yl]-3-[4-(2-(1-oxo-tetrahydrothiophen-3-yl)ethoxy)naphthalen-1-yl]-urea;
1-[5-tert-Butyl-2-p-tolyl-2H-pyrazol-3-yl]-3-[4-(3-morpholin-4-yl-propyl)naphthalen-1-yl]-urea;
1-[5-tert-Butyl-2-p-tolyl-2H-pyrazol-3-yl]-3-[4-(morpholin-4-yl-methyl)naphthalen-1-yl]-urea;
1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(piperdin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;

1-[5-tert-Butyl-2-p-tolyl-2H-pyrazol-3-yl]-3-[4-(2-(3,4-dimethoxyphenyl)-ethoxy)naphthalen-1-yl]-urea;

1-[5-tert-Butyl-2-p-tolyl-2H-pyrazol-3-yl]-3-[4-(pyridin-4-yl-methylamino)naphthalen-1-yl]-urea;

1-[5-iso-Propyl-2-phenyl-2H-pyrazol-3-yl]-3-[4-(2-morpholin-4-yl-ethoxy)naphthalen-1-yl]-urea;

1-[5-cyclohexyl-2-phenyl-2H-pyrazol-3-yl]-3-[4-(2-morpholin-4-yl-ethoxy)naphthalen-1-yl]-urea;

1-[5-(2,2,2-trifluoroethyl)-2-phenyl-2H-pyrazol-3-yl]-3-[4-(2-morpholin-4-yl-ethoxy)naphthalen-1-yl]-urea;

1-[5-(1-methylcycloprop-1-yl)-2-phenyl-2H-pyrazol-3-yl]-3-[4-(2-morpholin-4-yl-ethoxy)naphthalen-1-yl]-urea;

1-[5-(1-methylcyclohex-1-yl)-2-phenyl-2H-pyrazol-3-yl]-3-[4-(2-morpholin-4-yl-ethoxy)naphthalen-1-yl]-urea;

1-[5-tert-butyl-2-methyl-2H-pyrazol-3-yl]-3-[4-(2-morpholin-4-yl-ethoxy)naphthalen-1-yl]-urea;

1-[5-tert-butyl-2-(4-chlorophenyl)-2H-pyrazol-3-yl]-3-[4-(2-morpholin-4-yl-ethoxy)naphthalen-1-yl]-urea;

1-[5-tert-butyl-2-butyl-2H-pyrazol-3-yl]-3-[4-(2-morpholin-4-yl-ethoxy)naphthalen-1-yl]-urea;

1-[5-tert-butyl-2-(4-methyl-3-carbamylphenyl)-2H-pyrazol-3-yl]-3-[4-(2-morpholin-4-yl-ethoxy)naphthalen-1-yl]-urea;

1-[5-tert-butyl-2-(4-methyl-3-(morpholin-4-yl)methylphenyl)-2H-pyrazol-3-yl]-3-[4(2-morpholin-4-yl-ethoxy)naphthalen-1-yl]-urea;

1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;

1-[5-tert-butyl-2-(3-dimethylaminomethylphenyl)-2H-pyrazol-3-yl]-3-[4-(2-morpholin-4-yl-ethoxy)naphthalen-1-yl]-urea;

1-[5-tert-butyl-2-(2-chloropyridin-5-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-morpholin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea;

1-[5-tert-butyl-2-(pyridin-3-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;

1-[5-tert-butyl-2-(2-methylpyridin-5-yl)-2H-pyrazol-3-yl]-3-[4-(3-morpholin-4-yl-propyn-1-yl)naphthalen-1-yl]-urea.

Particularly preferred compounds of the formula(I) are:

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea or 1-[5-tert-butyl-2-methyl-2H-pyrazol-3-yl]-3-[4-(2-morpholin-4-yl-ethoxy)naphthalen-1-yl]-urea.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

The term "aroyl" as used in the present specification shall be understood to mean "benzoyl" or "naphthoyl".

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

The term "metabolite" shall be understood to mean any of the compounds of the formula (I) which are capable of being hydroxylated or oxidized, enzymatically or chemically, as will be appreciated by those skilled in the art. Nonlimiting examples of metabolites of the formula (I) are shown in the table below:

| Structure | Name |
|---|---|
| 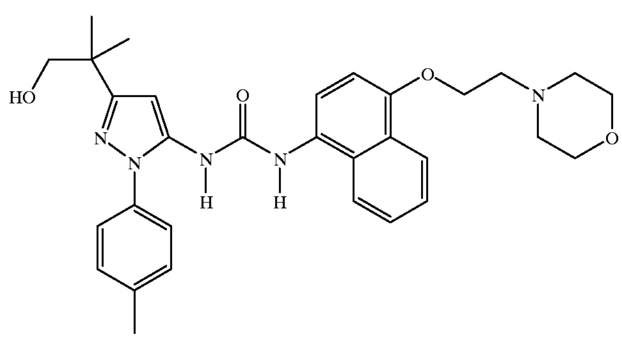 | 1-[5-(2-hydroxy-1,1 dimethyl-ethyl)-2-p-tolyl-2H-pyrazol-3-yl]-3-[4-(2-morpholin-4-yl-ethoxy)-naphthalen-1-yl]-urea |

-continued

| Structure | Name |
|---|---|
| 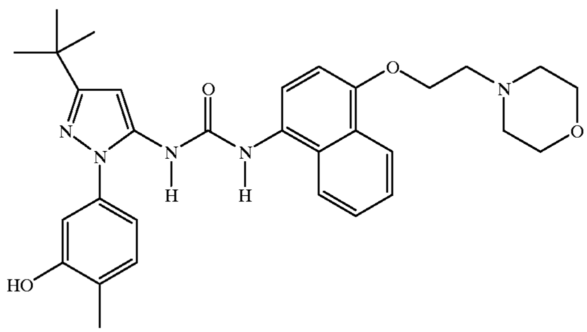 | 1-[5-tert-butyl-2-(3-hydroxy-4-methyl-phenyl)-2H-pyrazol-3-yl]-3-[4-(2-morpholin-4-yl-ethoxy)]naphthalen-1-yl]-urea |
| 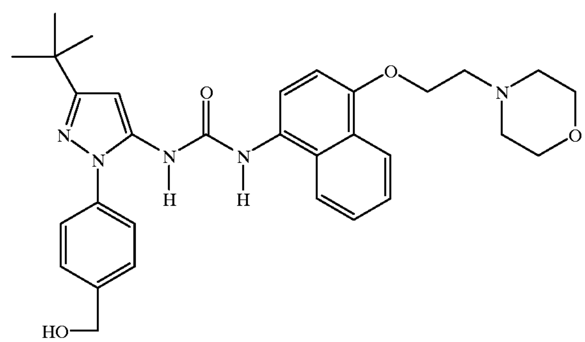 | 1-[5-tert-butyl-2-(4-hydroxymethyl phenyl)-2H-pyrazol-3-yl]-3-[4-(2-morpholin-4-yl-ethoxy)-naphthalen-1-yl]-urea |
| 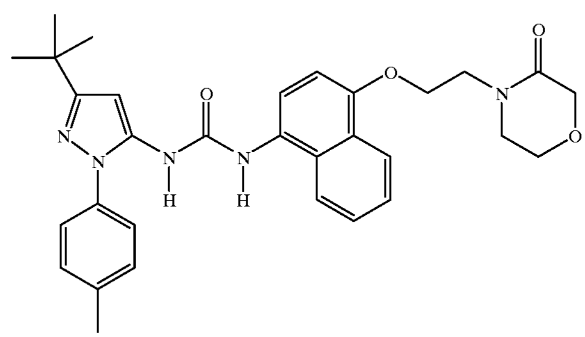 | 1-[5-tert-butyl-2-p-tolyl-2H-pyrazol-3-yl) 3-{4-[2-(3-oxo-morpholin-4-yl)-ethoxy] naphthalen-1-yl}-urea |
| 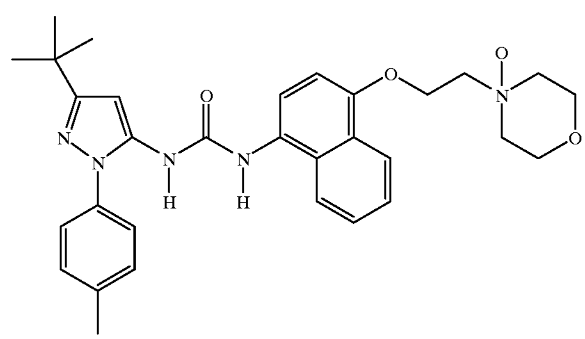 | 1-[5-tert-butyl-2-p-tolyl-2H-pyrazol-3-yl) 3-{4-[2-(4-hydroxy-morpholin-4-yl)-ethoxy]-naphthalen-1-yl}-urea |

-continued

| Structure | Name |
|---|---|
| 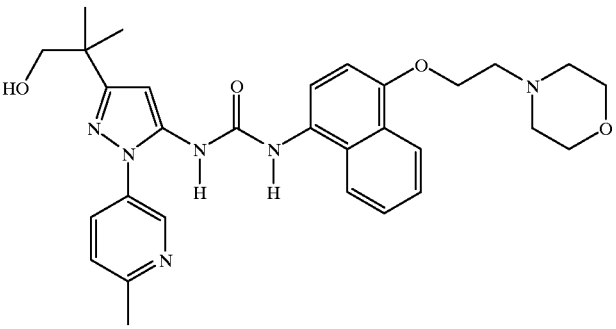 | 1-[5-(2-hydroxy-1,1-dimethyl-ethyl)-2-(6-methyl-pyridin-3-yl)-2H-pyrazol-3-yl]-3-[4-(2-morpholin-4-yl-ethoxy)-naphthalen-1-yl]-urea |
| 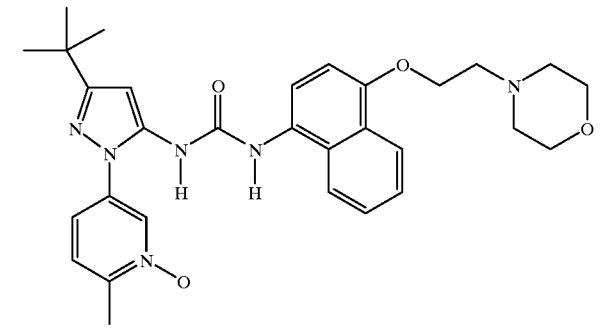 | 1-[5-tert-butyl)-2-(1-hydroxy-6-methyl-pyridin-3-yl)-2H-pyrazol-3-yl]-3-[4-(2-morpholin-4-yl-ethoxy)-naphthalen-1-yl]-urea |
| 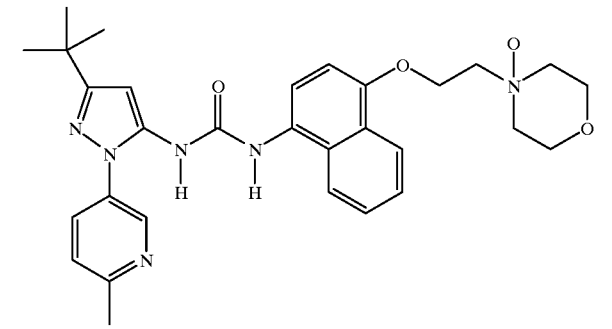 | 1-[5-tert-butyl)-2-(6-methyl-pyridin-3-yl)-2H-pyrazol-3-yl]-3-{4-[2-(4-hydroxy-morpholin-4-yl)-ethoxy]-naphthalen-1-urea |
| 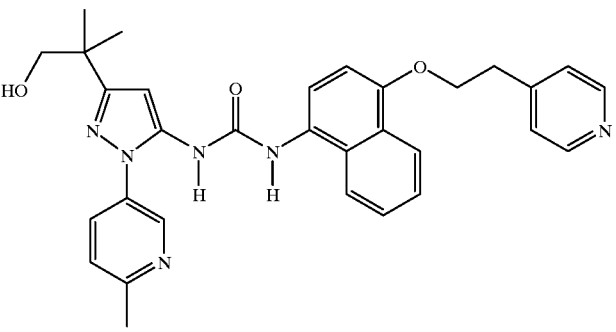 | 1-[5-(2-hydroxy-1,1-dimethyl-ethyl)-2-(6-methyl-pyridin-3-yl)-2H-pyrazol-3-yl]-3-[4-(2-pyridin-4-yl-ethoxy)-naphthalen-1-yl]-urea |

-continued

| Structure | Name |
|---|---|
| 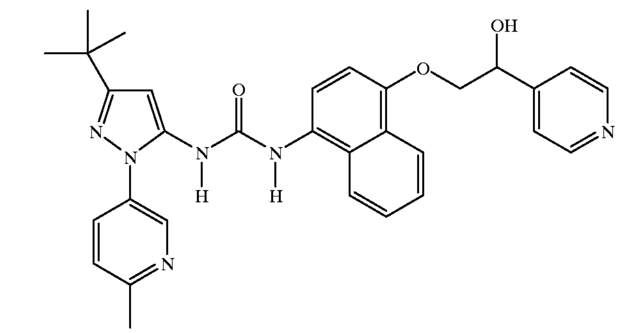 | 1-[5-(2-hydroxy-1,1-dimethyl-ethyl)-2-(6-2H-pyrazol-3-yl]-3-[4-(2-hydroxy-2-pyridin-4-yl-ethoxy)-naphthalen-1-yl]-urea |
| 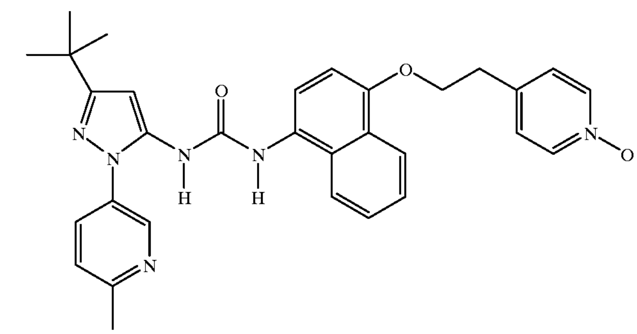 | 1-[5-tert-butyl)-2-(6-methyl-pyridin-3-yl)-2H-pyrazol-3-yl]-3-{4-[2-(1-hydroxy-pyridin-4-yl)-ethoxy]-naphthalen-1-yl}-urea |
| 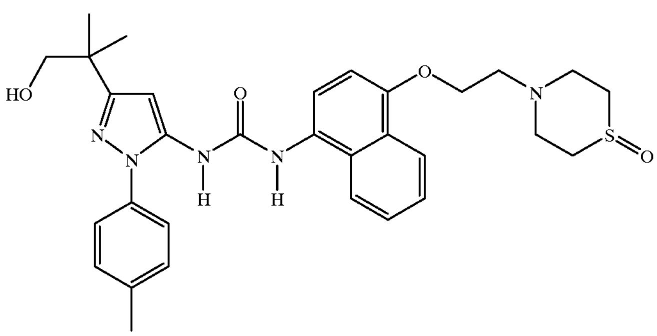 | 1-[5-(2-hydroxy-1,1-dimethyl-ethyl)-2-p-tolyl-2H-pyrazol-3-yl]-3-{4-[2-(1-oxo-thiomorpholin-4-yl)-ethoxy]-naphthalen-1-yl}-urea |
| 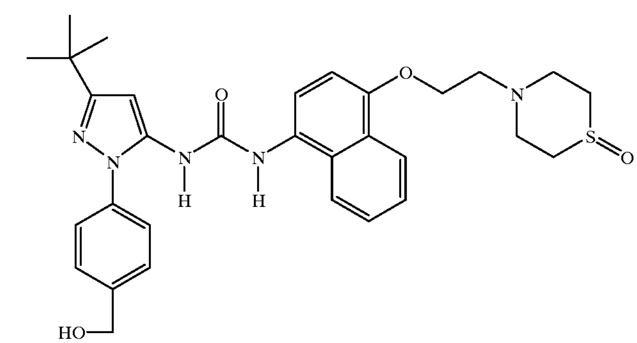 | 1-[5-tert-butyl-2-(4-hydroxymethyl-phenyl)-2H-pyrazol-3-yl]-3-{4-[2-(1-oxo-thiomorpholin-4-yl)-ethoxy]-naphthalen-1-yl}-urea |

-continued

| Structure | Name |
|---|---|
| 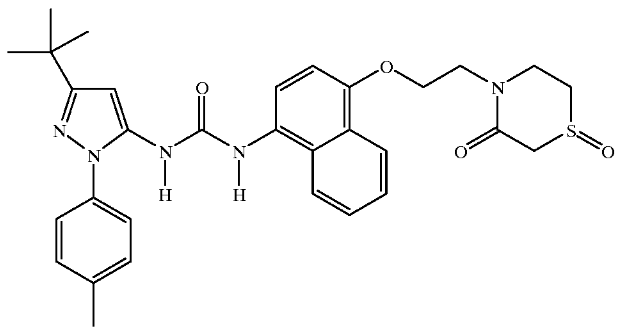 | 1-[5-tert-butyl-2-p-tolyl-2H-pyrazol-3-yl]-3-{4-[2-(1,3-dioxo-thiomorpholin-4-yl)-ethoxy]-naphthalen-1-yl}-urea |
| 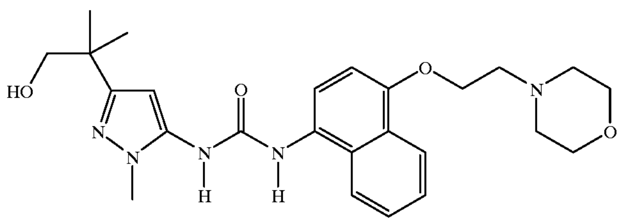 | 1-[5-(2-hydroxy-1,1-dimethyl-ethyl)-2-methyl-2H-pyrazol-3-yl]-3-[4-(2-morpholin-4-yl-ethoxy)-naphthalen-1-yl]-urea |
| 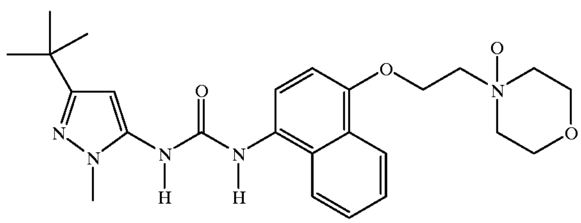 | 1-[5-tert-butyl-2-methyl-2H-pyrazol-3-yl]-3-{4-[2-(4-hydroxy-morpholin-4-yl)-ethoxy]-naphthalen-1-yl}-urea |

Pharmaceutically acceptable salts of the compounds of this invention include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4^+$ salts.

In addition, the compounds of this invention include prodrugs of compounds of the formula (I). Prodrugs include those compounds that, upon simple chemical transformation, are modified to produce a compound of formula (I). Simple chemical transformations include hydrolysis, oxidation and reduction. Specifically, when a prodrug of this invention is administered to a patient, the prodrug may be transformed into a compound of formula (I), thereby imparting the desired pharmacological effect.

GENERAL SYNTHETIC METHODS

The compounds of the invention may be prepared by Method A, B, or C as illustrated in Scheme I, preferably method C.

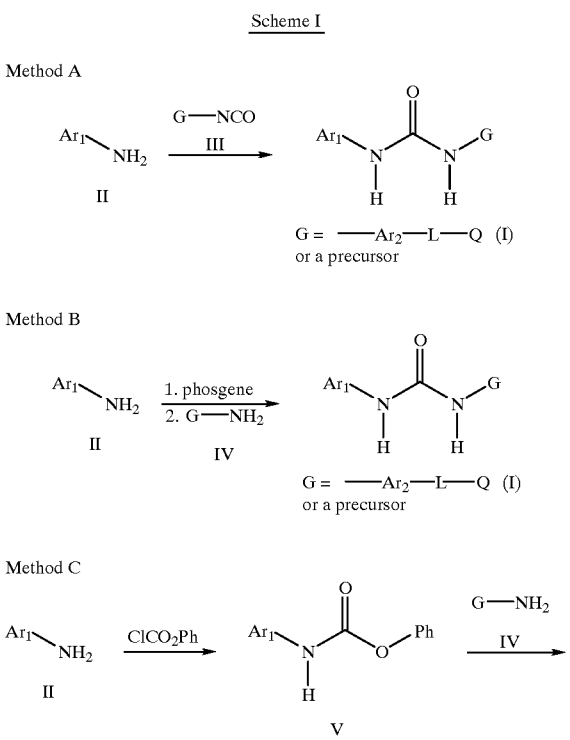

Scheme I

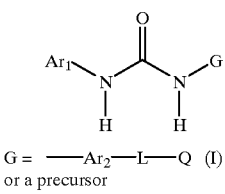

G = —Ar₂—L—Q  (I)
or a precursor

In Method A, a mixture of an aminoheterocycle of formula II and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 hr, and the volatiles are removed. Purification of the residue by recrystallization from an appropriate solvent such as ethyl acetate/hexanes, ethyl acetate/methanol, THF/petroleum ether, ethanol/water or by silica gel chromatography, using for example, hexanes and ethyl acetate as eluents, provides the product of formula I.

In Method B, an aminoheterocycle of formula II is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate of formula II. The isocyanate and arylamine IV are mixed in a non-protic, anhydrous solvent such as THF, ether, toluene, dioxane, methylene chloride or ethyl acetate. The preferred solvent is THR. The mixture is stirred at between 0–45° C., preferably at 25° C., for 2–24 hr, and the volatiles are removed. Purification of the residue by recrystallization or by silica gel chromatography, as above, provides the product of formula I.

In Method C, an aminoheterocycle of formula II is dissolved in a halogenated solvent, such as methylene chloride, chloroform or dichloroethane. The preferred solvent is methylene chloride. A suitable base such as triethylamine may be added, followed by phenyl chloroformate. The mixture is stirred at between 0–85° C., preferably at reflux temperature, for 2–24 hr, and the volatiles are removed providing carbamate V. The carbamate and arylamine IV are mixed in a non-protic, anhydrous solvent such as THF, ether, toluene, dioxane, methylene chloride or ethyl acetate. The preferred solvent is THF. The mixture is stirred at between 0–10° C., preferably at reflux temperature, for 2–24 hr, and the volatiles are removed. Purification of the residue as above provides the product of formula I.

The method used to produce an aminoheterocycle of formula II will depend on the nature of the desired heterocycle. In general, intermediates of formula II can be made by methods known to those skilled in the art. Some general methods are illustrated in the schemes below. Compounds G—NCO or G—N.H.₂ in Scheme I may be commercially available, or may be prepared by methods known to those skilled in the art. If G is a precursor of $Ar_2$-L-Q, the desired final product of formula (I) may be constructed by methods known to those skilled in the art. Illustrative examples are contained in the Synthetic Examples section below.

Desired aminopyrazoles of formula XIII can be prepared as described in Scheme II. A hydrazine of formula VIII, bearing substituent $R_3$, may be prepared by Method D or E. In Method D, an aryl bromide of formula VI is dissolved in a non-protic, inert solvent, such as THF, 1,4-dioxane or diethyl ether, and cooled to low temperature under an inert atmosphere. The preferred temperature for the solution is –77° C. A strong base dissolved in a non-protic, inert solvent, such as hexanes, THF or ether, is added dropwise while maintaining a reaction temperature below 0° C. and preferrably below –60° C. The preferred bases are alkyl lithium reagents and the most preferred is sec-butyl lithium. After the addition of the base, the reaction mixture is stirred for a period of time between thirty and ninety minutes or until all the starting aryl bromide has been consumed. An excess of dialkyl azodicarboxylate is added while maintaining a reaction temperature below 0° C. and preferably below –60° C. The preferred dialkyl azodicarboxylate is di-tert-butyl azodicarboxylate. The reaction is stirred at cold temperatures and warmed to room temperature after 0.5 hr to 2 hr. The reaction is quenched with the addition of water and the product extracted into a non-protic solvent, such as ethyl acetate, diethyl ether or chloroform. The organic layers are dried with agents such as $MgSO4$ or $Na_2SO_4$, and the volatiles removed. The residue is dissolved in protic solvents, such as methanol or iso-propanol, cooled, preferably to 0–5° C. and treated with acid. Preferred acids are hydrochloric, hydrobromic, sulfuric and trifluoroacetic. The most preferred is hydrochloric in gaseous form. After the addition of excess acid the mixture is heated at the reflux temperature of the solvent until all starting material has been consumed. After cooling the product aryl-hydrazine of formula VIII salt is filtered and dried.

Scheme II

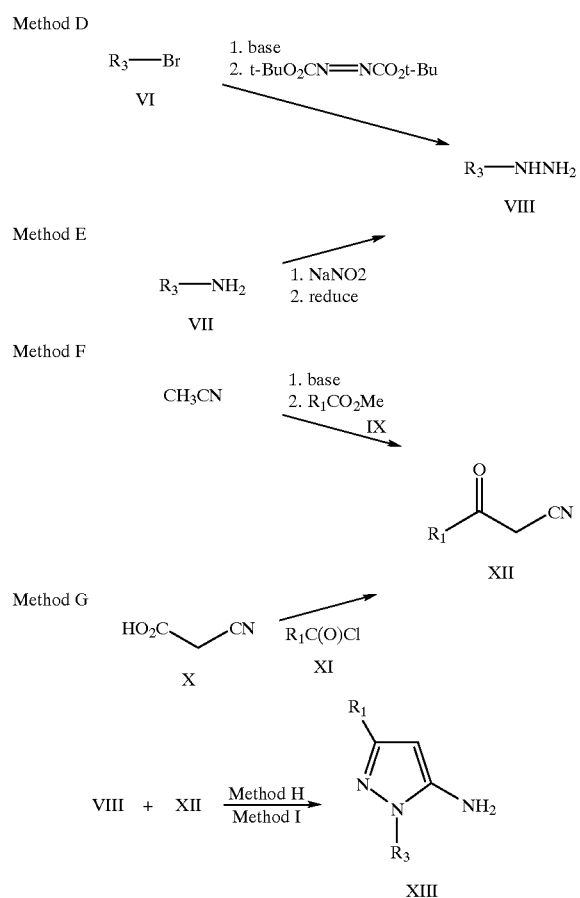

In Method E, an aryl amine bearing $R_3$ of formula VII is dissolved in a concentrated aqueous acid such as hydrochloric, hydrobromic or sulfuric and cooled to ice bath temperatures. The most preferred acid is hydrochloric with concentrations between 3–8N with the most preferred concentration of 6N. A nitrosating reagent in water is added dropwise while maintaining a cold temperature. The preferred temperature is 0–5° C. The preferred reagent is sodium nitrite. The reaction is stirred between 10–90 min and a reducing agent is added while maintaining cold temperatures. The preferred temperature is 0–5° C. Reducing agents include zinc, iron, samarium iodide and tin(II) chloride. The most preferred agent is tin(II) chloride dissolved in aqueous hydrochloride with a concentration of 3–8 N with a most preferred concentration of 6N The reaction is stirred between 0.5–3 hr and quenched with alkali to a pH between 12–14. Alkali reagents include sodium hydroxide, potassium hydroxide, lithium hydroxide and calcium hydroxide. The most preferred alkali reagent is potassium hydroxide. The aqueous solution is extracted with a non-protic organic solvent, such as diethyl ether, chloroform, ethyl acetate and methylene chloride. The organic layers are dried with agents such as $MgSO_4$ and $Na_2SO_4$ and the volatiles removed to provide the aryl-hydrazine (VIII) which can be carried forward without further purification.

A β-ketonitrile bearing $R_1$ (XII) may be prepared by Method F or G. In Method F, a metal hydride, such as sodium hydride, potassium hydride or lithium hydride, is suspended in an anhydrous, inert, non-protic solvent, such as diethyl ether, THF and dioxane, at temperatures between 35–85° C. The most preferred metal hydride is sodium hydride and the most preferred solvent is THF at a temperature of 75° C. An alkyl ester, preferably a methyl ester (IX), and acetonitrile is dissolved in an anhydrous, inert, non-protic solvent such as diethyl ether, THF or dioxane and added dropwise to the metal hydride suspension. The preferred solvent is THF. The mixture is kept at elevated temperatures between 3–24 hours, cooled to room temperature and diluted with a non-protic solvent and aqueous acid. The organic layer is washed with water and brine, dried, with agents such as $MgSO_4$ and $Na_2SO_4$, and the volatiles removed to provide the β-ketonitrile (XII) which could be used without further purification.

Alternatively, following Method G, a solution of a strong base, such as alkyl lithium reagents and metal amide reagents, such as n-butyl lithium, sec-butyl lithium, methyl lithium and lithium diisopropylamide, in an anhydrous, inert, non-protic solvent, such as diethyl ether, THF and dioxane, is cooled below 0° C. The preferred base is n-butyl lithium, the preferred solvent is THF and the preferred temperature is −77° C. A solution of cyanoacetic acid (X) in an anhydrous, inert, non-protic solvent, such as diethyl ether, THF and dioxane, and most preferrably THF, is added dropwise while maintaining a reaction temperature below 0° C. and preferrably at −77° C. The reaction is stirred between 10–45 min while warming to 0° C. The solution of the dianion of cyanoacetic is cooled to temperatures below −25° C. and preferrably at −77° C. An alkyl acid chloride (XI) dissolved in an anhydrous, inert, non-protic solvent, such as diethyl ether, THF and dioxane, and most preferrably THF, is added. The reaction mixture is warmed to 0° C. between 10–30 min. and quenched with aqueous acid. The product is extracted with an organic solvent such as chloroform, ethyl acetate, ether and methylene chloride. The combined organic extracts are dried, with agents such as $MgSo_4$ and $Na_2SO_4$, and the volatiles removed to provide the β-ketonitrile (XII) which could be used without further purification.

The desired aminopyrazole (XIII) may then be prepared by Method H or I. In Method H, aryl hydrazine VIII and β-ketonitrile XII are mixed in an organic solvent, such as toluene, ethanol, iso-propanol or t-butanol. The preferred solvent is ethanol. An acid, such as hydrochloric acid, p-toluene sulfonic acid or sulfuric acid, is added, The preferred acid is concentrated hydrochloric acid. The mixture is heated to temperatures between 50–100° C., preferrably at 80° C., for 10–24 hr and cooled to room temperature. The mixture is diluted with non-protic organic solvent, such as ethyl acetate, ether, chloroform and methylene chloride, and washed with aqueous alkali, such as sodium bicarbonate and potassium carbonate. The organic layer is dried, with agents such as $MgSO_4$ and $Na_2SO_4$, and the volatiles removed to provide a residue which is purified by recrystallization or silica gel chromatography using hexanes and ethyl acetate as eluents. The product-rich fractions are collected and the volatiles removed to provide the desired amonopyrazole (XIII).

Alternatiavely, using Method I, aryl hydrazine VIII and β-ketonitrile XII are mixed in an organic solvent, such as toluene, ethanol, iso-propanol or t-butanol. The preferred solvent is toluene. The mixture is heated at reflux temperatures for 3–24 hrs with azeotropic removal of water and worked up as described above providing the aminopyrazole XIII.

A general synthesis for desired aminothiophenes is illustrated in Scheme III, Method J.

Scheme III

Method J

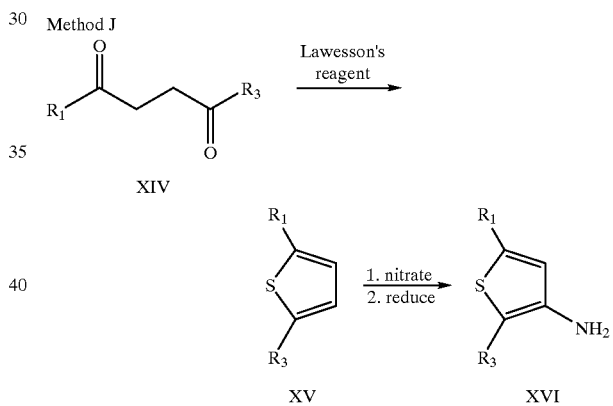

A mixture of 1-aryl-5-alkyl-butane-1,4-dione (XIV) and a sulfating reagent, such as Lawesson's reagent or phosphorous (V) sulfide, and preferrably Lawesson's reagent, is dissolved in a non-protic, anhydrous solvent, such as toluene, THF and dioxane. The preferred solvent is toluene. The mixture is heated at elevated temperatures and preferably at a solvent-refluxing temperature for 1–10 hr. The volatiles are removed and the residue is purified by silica gel chromatography using hexanes and ethyl acetate as eluent. The product-rich fractions are collected and the volatiles removed to provide the substituted thiophene XV.

A mixture of substituted thiophene XV is dissolved in a solvent such as acetic anhydride or acetic acid. The preferred solvent is acetic anhydride. The mixture is cooled to 0–30° C. and preferrably to −10° C. A solution of concentrated nitric acid in a solvent such as acetic anhydride or acetic acid, with the preferred solvent being acetic anhydride is added while cooling 0–30° C. and preferrably to −10° C. The mixture is stirred between 10–120 min, poured onto ice and extracted with a non-protic solvent such as diethyl ether, chloroform, ethyl acetate or methylene chloride. The organic extracts are washed with aqueous alkali, dried with agents such as $MgSO_4$ and $Na_2SO_4$ and the volatiles removed. The residue is purified by silica gel chromatography using hexanes and ethyl acetate as eluents. The product-rich fractions are collected and the volatiles removed to provide the 2-aryl-5-alkyl-3-nitrothiophene. The 2-aryl-5-alkyl-3-nitrothiophene is reduced by metals, such as iron, tin and zinc or catalytic hydrogenation. The preferred reduction occurs with iron in acetic acid at temperatures between 50–110° C. and preferrably at 100° C. for 5–30 min. After cooling to room temperature the reaction is diluted with water, neutralized with alkali, such as sodium hydroxide, potassium hydroxide, potassium carbonate or sodium bicarbonate, and extracted with a non-protic solvent such as diethyl ether, ethyl acetate or methylene chloride. The organic extracts are dried with agents such as $MgSO_4$ and $Na_2SO_4$ and the volatiles removed to provide the desired aminothiophene XVI.

Other desired aminoheterocycles can be prepared by methods known in the art and described in the literature. The examples that follow are illustrative and, as recognized by one skilled in the art, particular reagents or conditions could be modified as needed for individual compounds. Intermediates used in the schemes below are either commercially available or easily prepared from commercially available materials by those skilled in the art.

Scheme IV outlines a general scheme for desired aminofurans as described by Stevenson et al. (J. Am. Chem. Soc., 1937, 59, 2525). An ethyl aroylacetate (XVII) is dissolved in a non-protic solvent, such as ether or THF, and treated with a strong based, such as sodium, sodium ethoxide or sodium hydride, and the anion is reacted with a bromomethyl alkylketone (XVIII) at low temperatures, such as 0° C. After stirring the reaction until no starting material remains, it is poured onto cold water and extracted with a non-protic solvent. The combined extracts are dried with agents such as $MgSO_4$ or $Na_2SO_4$. The diketo-ester (XIX) may be carried forward without further purification or purified by distillation or silica gel chromatography. The diketo-ester in a protic solvent, such as ethanol, is heated in the presence of a mineral acid, such as sulfuric or hydrochloric, for 5–10 hr. and extracted with a non-protic solvent. The combined extracts are dried with agents such as $MgSO_4$ or $Na_2SO_4$. The furan-ester (XX) may be carried forward without further purification or purified by distillation or silica gel chromatography. The furan-ester in a protic solvent, such as ethanol, is treated with hydrazine hydrate and the mixture heated for 2–5 days. The hydrazide is isloated as above and treated with hot formic acid and the resulting furan-amine (XXI) purified by distillation or silica gel chromatography.

Scheme IV

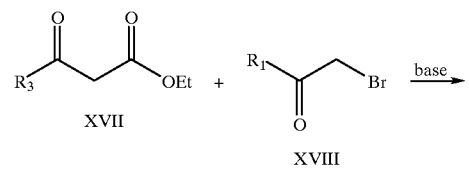

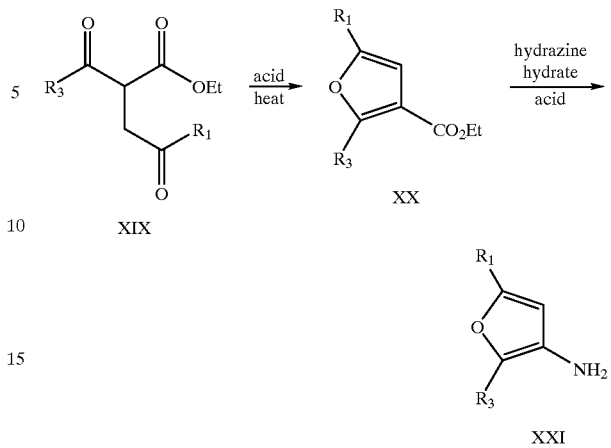

The synthesis of substituted 4-aminooxazoles may be achieved analogous to a procedure described by Lakhan et al. (J. Het. Chem., 1988, 25, 1413) and illustrated in Scheme V. A mixture of aroyl cyanide (XXII), aldeyde (XXIII) and anhydrous ammonium acetate in acetic acid is heated at 100–110° C. for 3–6 hr, cooled to room temperature and quenched with water. Extraction by a non-protic solvent provides the product XXIV which can be carried forward without further purification or purified by recrystallization or silica gel chromatography.

Scheme V

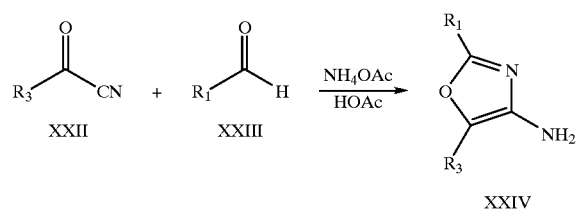

The synthesis of substituted 3-aminopyrroles (XXVIII) may be achieved in a manner analogous to Aiello et al., J. Chem. Soc. Perkins Trans. I, 1981, 1. This is outlined in Scheme VI. A mixture of aryldioxoalkane (XXV) and amine (XXVI) in acetic acid is heated at 100–110° C. for 3–6 hr and worked up in the usual manner. The product (XXVII) in acetic acid is treated with a nitrating agent, such as nitric acid and potassium nitrate in concentrated sulfuric acid. The mixture is poured onto cold water and extracted with a non-protic solvent. The combined extracts are dried with agents such as $MgSO_4$ and $Na_2SO_4$. Removal of the volatiles provides the nitro-pyrrole which which may be carried forward without further purification or purified by recrystallization or silica gel chromatography. The nitro-pyrrole is reduced to the amine with iron in acetic acid or by catalytic hydrogenation using palladium on activated carbon. The aminopyrrole (XXVIII) may be carried forward without further purification or purified by recrystallization or silica gel chromatography.

Scheme VI

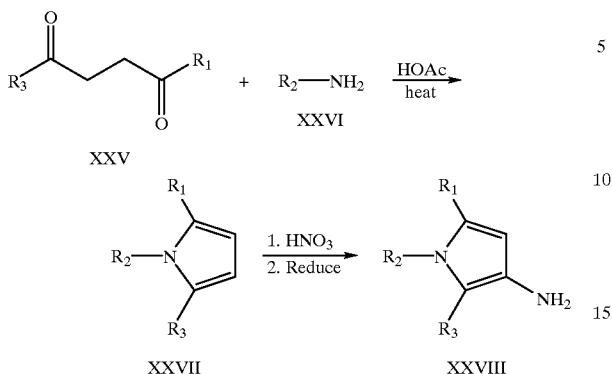

Scheme VIII

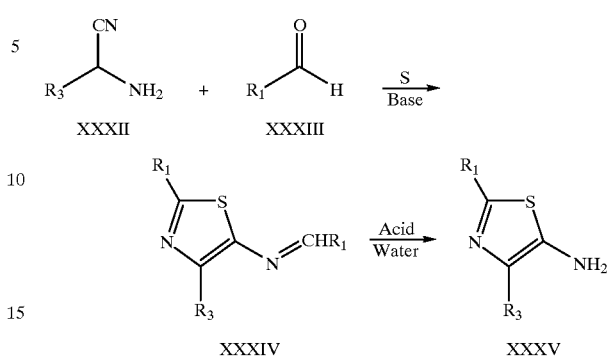

In an analogous fashion, a mixture of amine XXIX and 3-aryl-2,5-dioxoalkane (XXX) in acetic acid is heated between 80–110° C. for 2–24 hr. The reaction is diluted with water and extracted with an organic solvent. The combined extracts are dried with agents such as $MgSO_4$ or $Na_2SO_4$ and the volatiles removed. The resulting pyrrole is treated with a nitrating agent and subsequently reduced to XXXI as described above. The product may be carried forward without further purification or purified by recrystallization or silica gel chromatography. This process is illustrated is Scheme VII.

Scheme VII

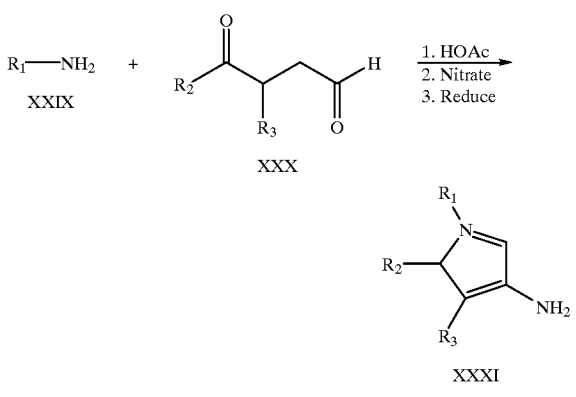

Substituted 5-aminothiazoles (XXXV) may be prepared in a manner analogous to Gerwald et al., J. Prakt. Chem. 1973, 315, 539. As illustrated in Scheme VIII, to a mixture of aminocyanide XXXII, aldehyde XXXIII and sulfur in an anhydrous solvent, such as ethanol and methanol, is added dropwise a base, such as triethylamine. The mixture is heated at 50° C. for 1–3 hr. The mixture is cooled and the excess sulfur removed. Acetic acid is added to neutralize the mixture and the solid collected. The imine XXXIV is treated with acid, such as hydrochloric and toluenesulfonic acid, in water and an organic solvent. After the starting material is consumed the reaction is worked up and the product XXXV may be carried forward without further purification or purified by recrystallization or silica gel chromatography.

A synthesis of substituted 2-aminothiophenes (XXXVII), analogous to a procedure described by Gewald et al. (J. Prakt. Chem., 1973, 315, 539) is illustrated in Scheme IX. A mixture of disubstituted thiophene-3-carboxylic acid (XXXVI) in a protic solvent, such as acetic acid, at a temperature of 0–50° C. is treated with a nitrating agent, such as nitric acid or potassium nitrate in concentrated sulfuric acid. After the starting material has been consumed the reaction is poured onto ice and the product extracted with a non-protic solvent. The combined extracts are dried with agents such as $MgSO_4$ and $Na_2SO_4$ and the volatiles removed. The nitrothiophene is reduced to the amine with iron in acetic acid or by catalytic hydrogenation using palladium on activated carbon. The amino-thiophene may be carried forward without further purification or purified by recrystallization or silica gel chromatography.

Scheme IX

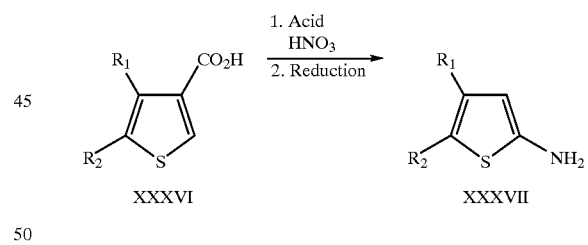

1,5-Disubstituted-3-aminopyrazoles (XL) may be prepared as shown in Scheme X, in a fashion analogous to the procedure described by Ege et al. (J. Het. Chem., 1982, 19, 1267). Potassium is added to anhydrous t-butanol and the mixture cooled to 5° C. Hydrazine XXXVIII is added, followed by cyanodibromoalkane XXXIX. The mixture is heated at refluxing temperatures for 3–10 hr. The mixture is cooled to room temperature and poured onto ice water. The product is extracted with an organic solvent. The combined extracts are dried with agents such as $MgSo_4$ or $Na_2SO_4$ and the volatiles removed. The product XL may be carried forward without further purification or purified by recrystallization or silica gel chromatography.

Scheme X

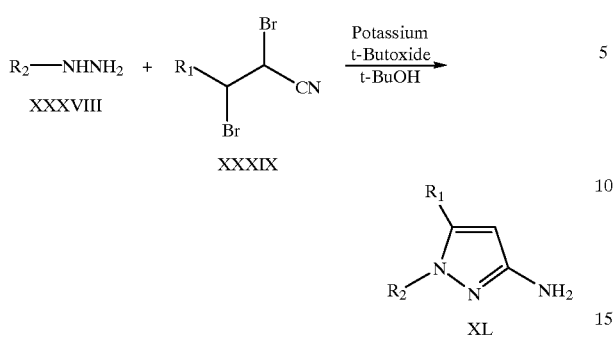

Scheme XII

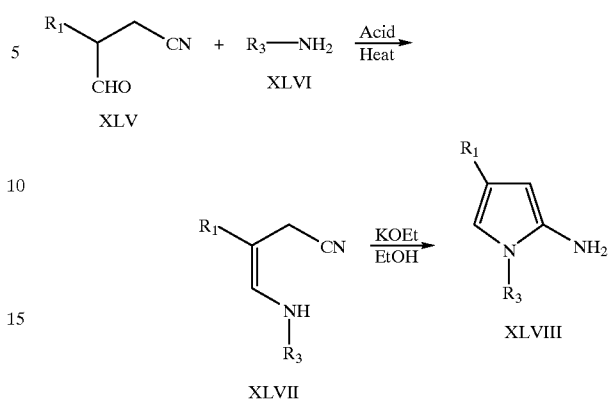

The synthesis of 2-amino-3,5-disubstituted thiophenes shown in Scheme XI, is done in a fashion analogous to Knoll et al., *J. Prakt. Chem.*, 1985, 327, 463. A mixture of substituted N-(3-aminothioacryloyl)-formamidine (XLI) and substituted bromide (XLII) in a protic solvent, such as methanol or ethanol, is heated, preferably at a reflux temperature, for 5–30 min and cooled below room temperature. The product thiophene-imine is filtered and dried. The thiophene-imine XLIII is converted to the thiophene-amine (XLIV) by treatment with aqueous acid.

Scheme XI

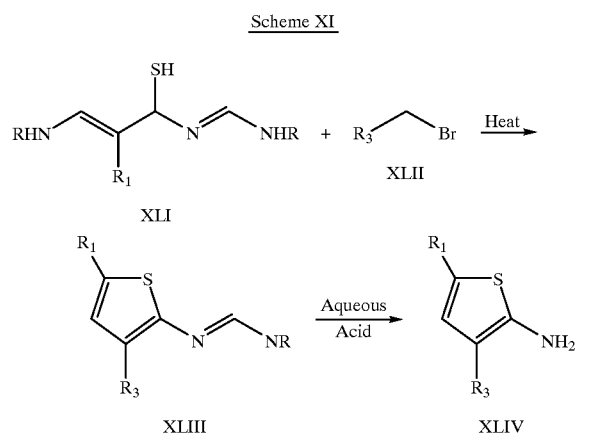

The synthesis of 1,4-disubstituted-2-aminopyrroles (XLVIII) may be accomplished in a manner analogous to Brodrick et al. (*J. Chem. Soc. Perkin Trans. I*, 1975, 1910), and as illustrated in Scheme XII. The potassium salt of formylnitrile XLV in water is treated with amine XLVI and acetic acid and the mixture heated at 50–90° C. for 5–30 min. The aminonitrile XLVII is collected by filtration upon cooling and then is stirred at room temperature with a base such as ethanolic potassium ethoxide for 2–5 hr and the volatiles removed. The residue is diluted with water and extracted with an organic solvent. The combined extracts are dried with agents such as $MgSO_4$ and $Na_2SO_4$ and the volatiles removed. The product (XLVIII) may be carried forward without further purification or purified by recrystallization or silica gel chromatography.

The preparation of 1,2-disubstituted-4-aminoimidaxoles (L) by reduction of the corresponding nitro compound (XLIX), for example with iron in acetic acid or catalytic hydrogenation may be accomplished as described by Al-Shaar et al. (*J. Chem. Soc. Perkin Trans. I*, 1992, 2779) and illustrated in Scheme XIII.

Scheme XIII

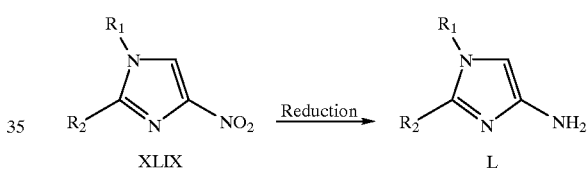

2,4-Disubstituted 5-aminooxazoles (LV) may be prepared in a manner analogous to the procedure described by Poupaert et al. (Synthesis, 1972, 622) and illustrated in Scheme XIV. Acid chloride LI is added to a cold mixture of 2-aminonitrile LII and a base such as triethylamine in a non-protic solvent, such as THF, benzene, toluene or ether. The preferred temperature is 0° C. The mixture is stirred for 12–24 hr and washed with water. The volatiles are removed and the product LIII treated with ethylmercaptan and dry hydrogen chloride in dry methylene chloride for 5–30 min. The solid 5-imino-1,3-oxazole hydrochloride (LIV) is collected by filtration, dissolved in dry pyridine and the solution saturated with hydrogen sulfide during 4 hr at 0° C. The mixture is diluted with an organic solvent and washed with water and dried. Removal of the volatiles provides the 5-amino-1,3-oxazole product (LV) which may be carried forward without further purification or be purified by silica gel chromatography.

Scheme XIV

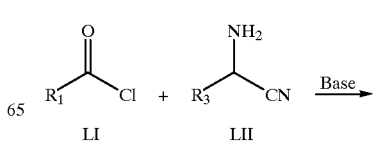

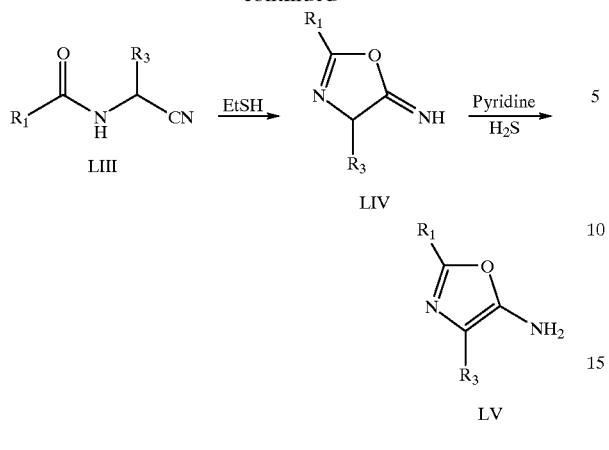

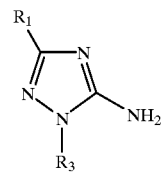

LVIII

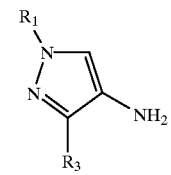

LIX

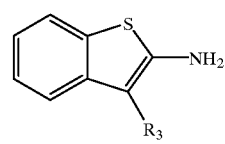

LX

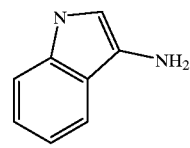

LXI

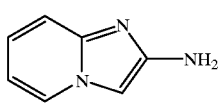

LXII

The synthesis of 1,4-disubstituted-2-aminopyrazoles may be accomplished as illustrated in Scheme XV and described in Lancini et al., *J. Het. Chem.*, 1966, 3, 152.

To a mixture of substituted aminoketone (LVI) and cyanamide in water and acetic acid was added aqueous sodium hydroxide until pH 4.5 is reached. The mixture is heated at 50–90° C. for 1–5 hr, cooled and basicified with ammonium hydroxide. The product LVII is collected by filtration and dried.

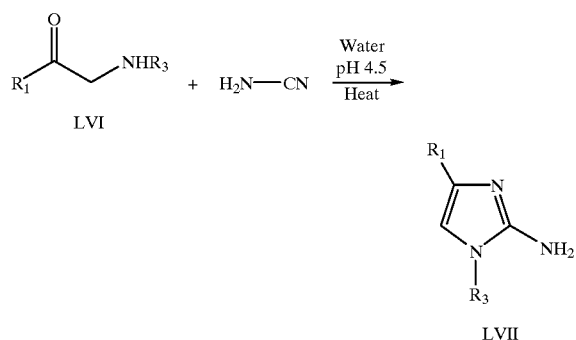

As in the cases described above, the synthesis of many other aminoheterocycles useful as intermediates may be accomplished by methods similar to those described in the literature or known to those skilled in the art. Several additional examples are illustrated in Scheme XVI. 2,5-Disubstituted-3-aminotriazoles (LVIII) have been described by Plenkiewicz et al. (*Bull. Chem. Soc. Blg.* 1987, 96, 675). 1,3-Disubstituted-4-aminopyrazoles (LIX) have been described by Guarneri et al. (*Gazz. Chim. Ital.* 1968, 98, 569). Damany et al. (*Tetrahedron*, 1976, 32, 2421) describe a 2-amino-3-substituted benzothiophene (LX). A 3-aminoindole (LXI) is described by Foresti et al.. (*Gazz. Chim. Ital.*, 1975, 125, 151). Bristow et al. (*J. Chem. Soc.*, 1954, 616) describe an imidazo[1,2-a]pyridin-2-yl amine (LXII).

METHODS OF THERAPEUTIC USE

The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Nalt. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly be neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula(I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

1-[5-tert-Butyl-2-p-tolyl-2H-pyrazol-3-yl]-3-[4-(2-morpholin-4-yl-ethoxy)naphthalen-1-yl]-urea:

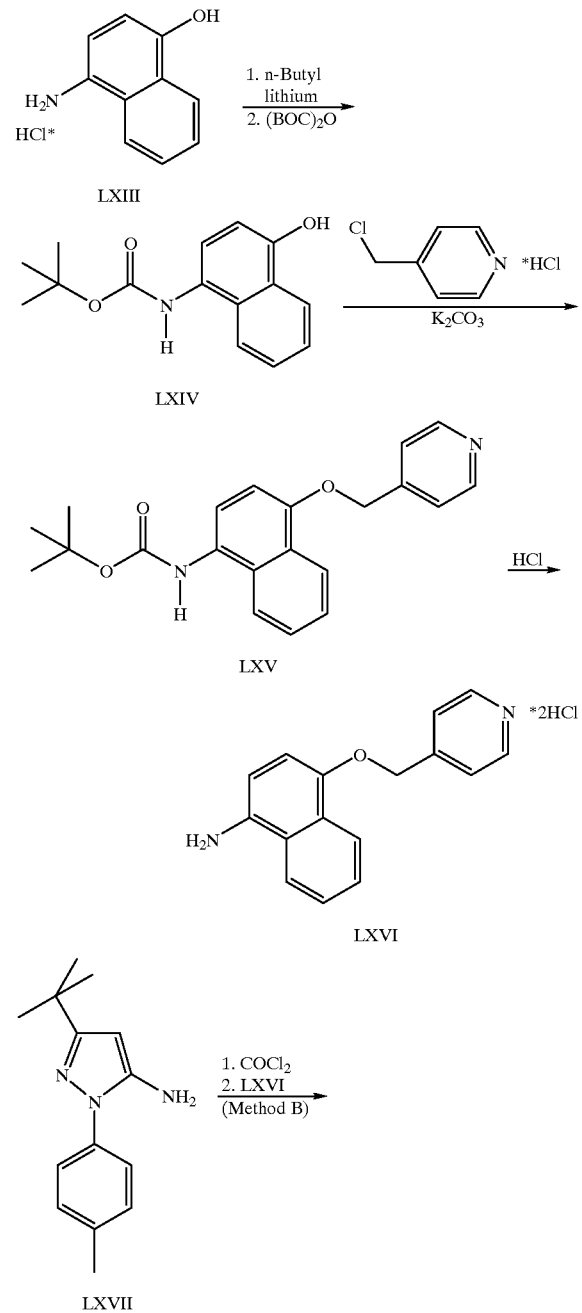

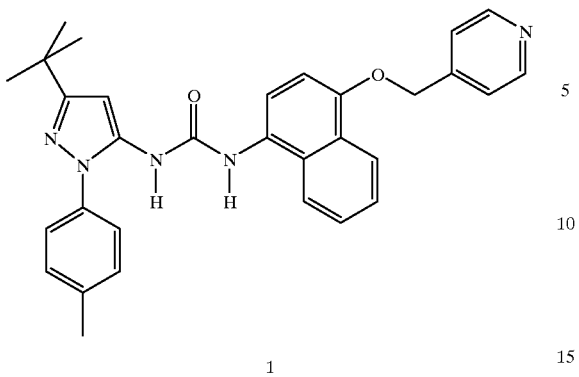

1

A mixture of 4-methylphenyl hydrazine hydrochloride (10.0 g) and 4,4-dimethyl-3-oxopentanenitrile (8.67 g) in 150 mL ethanol and 7 mL concentrated HCl was heated at reflux overnight, cooled to room temperature, basified to pH 12 with alkali and extracted with diethyl ether. The combined organic extracts were washed with brine and dried (MgSO$_4$). Removal of the volatiles in vacuo left a residue which was triturated with hot petroleum ether (100 mL) and provided 12.5 g of LXVII.

To a mixture of 4-amino-1-naphthol hydrochloride (LXIII) (172.1 g) in 750 mL anhydrous THF at −78° C. was added dropwise over 60 min n-butyl lithium (490 mL of a 1.60 M solution in hexanes). After the addition was complete the mixture was allowed to warm to room temperature and then cooled to −78° C. and di-tert-butyl dicarbonate ((BOC)$_2$O, 192 g) in 200 mL THF was added over 20 min. The mixture was slowly warmed to room temperature and stirred for 3 h and most of the volatiles removed in vacuo. The residue was diluted with ethyl acetate (1 L) and washed with water (2×200 mL) and brine (200 mL) and filtered through celite and dried (MgSO$_4$). Removal of the volatiles in vacuo provided LXIV (226.1 g).

A mixture of LXIV (0.397 g), 4-chloromethylpyridine hydrochloride (0.237 g) and potassium carbonate (0.996 g, powdered) in 10 mL of acetonitrile was heated at 80° C. for 6 hr, cooled to room temperature and diluted with water and ethyl acetate. The organic layer was washed with water and brine and dried (MgSO$_4$). Removal of the volatiles in vacuo and purification of the residue with flash chromatography using ethyl acetate as the eluent provided 0.277 g LXV. A mixture of LXV (0.26 g) and HCl (0.6 mL of 4M HCl in dioxane) in 5 mL dioxane was stirred at room temperature for 18 hr. Removal of the volatiles in vacuo provided LXVI.

As outlined in Method B (Scheme I), a mixture of LXVII (0.076 g) and phosgene (0.68 mL of a 1.93 M solution in toluene) in 10 mL methylene chloride and 10 mL saturated sodium bicarbonate was stirred rapidly for 15 min at 0–5° C. and the organic layer dried (MgSO$_4$). Removal of the volatiles in vacuo left a residue which was added to a mixture of the dihydrochloride salt from above (0.104 g) and N,N-di-iso-propylethylamine (0.32 mL) in 5 mL anhydrous THF. The mixture was stirred overnight and diluted with ethyl acetate and water. The organic layer was washed with water and brine and dried (MgSO$_4$). Removal of the volatiles in vacuo and purification of the residue with flash chromatography using ethyl acetate as the eluent and recrystallization of the solid with water and ethanol gave 1, m.p. 132–133° C.

Example 2

1-[5-tert-Butyl-2-p-tolyl-2H-pyrazol-3-yl]-3-[4-(3-(tetrahydropyran-2-yl-oxy)propyn-1-yl)naphthalen-1-yl]-urea:

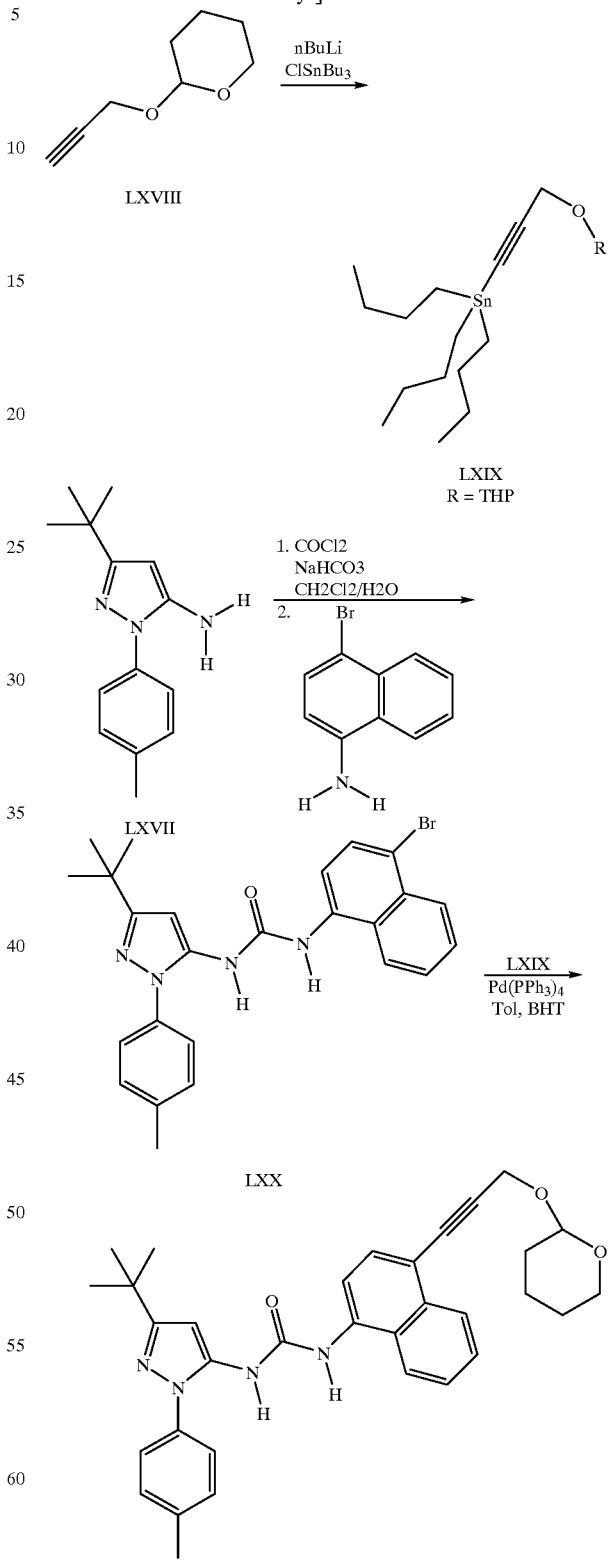

2

Tetrahydro-2-(2-propynyloxy)-2H-pyran (LXVIII) (2.50 mL; 17.8 mmol) in 100 mL anhydrous THF at −78° C. under inert atmosphere was treated with n-butyllithium (7.1 mL of a 2.5 M solution in hexanes), added via syringe. The reaction was warmed to −20° C. and after 1 h stirring, tributyltin chloride (4.8 mL, 17.8 mmol) was added. After stirring at −20° C. for 1 h the reaction mixture was quenched with dilute NaHCO$_3$ solution (~75 mL) and extracted with ethyl ether (3×50 mL). The combined ethereal extracts were washed to brine and dried (MgSO$_4$). After filtration all volatiles were removed in vacuo to produce LXIX as a yellow oil (4.7 g; 11.0 mmol or 62% yield).

A mixture LXVII (Example 1) (1.00 g; 3.76 mmol) and phosgene (5.6 mL of a 2 M solution in toluene) and 4-bromonaphthylamine were reacted according to Method B (Scheme I and Example 1). The product was purified by trituration with hot heptane to afford LXX, mp 193–194° C. (1.75 g, 3.67 mmol, 97% yield).

A mixture of LXX (970 mg, 2.03 mmol) and LXIX (1.31 g, 3.05 mmol) and BHT (50 mg) in 50 mL toluene at reflux under inert atmosphere was treated with tetrakis (triphenylphosphine)palladium(0) (350 mg, 0.305 mmol). The reaction mixture slowly changed color to black. After 40 min heating was stopped and, when the reaction mixture had cooled to ambient temperature, a 5 M aqueous solution of KF (~75 mL) was added. The mixture was stirred vigorously for 6 h, then the product was extracted with ethyl acetate (3×50 mL). The combined organic extracts were washed with brine and dried (MgSO$_4$), filtered and all volatiles were removed in vacuo. Column chromatography, using 25% ethyl acetate in hexane eluant, followed by recrystallization from hot ethyl acetate/hexane afforded 780 mg of 2, mp 159–160° C., (1.45 mmol, 72% yield).

Example 3

1-[5-tert-butyl-2-p-tolyl-2H-pyrazol-3-yl]-3-[4-(3-pyridin-4-yl-propoxy)naphthalen-1-yl]-urea (3):

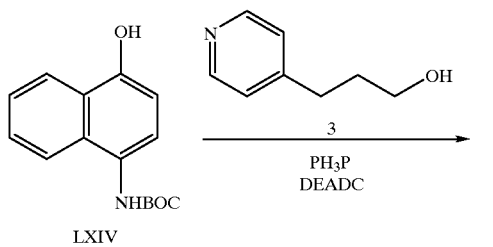

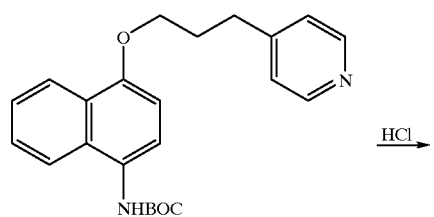

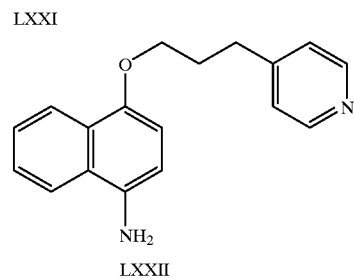

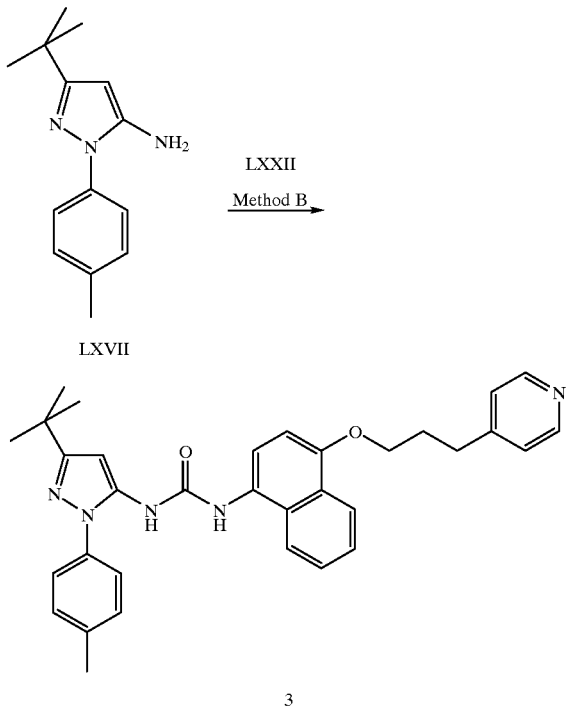

To a mixture of LXIV (Example 1) (0.51 g), 4-pyridinyl-1-propanol (0.76 mL), and triphenylphosphine (1.5 g) in 10 mL anhydrous THF was added dropwise diethyl azodicarboxylate (DEADC, 0.90 mL). After stirring overnight, the volatiles were removed in vacuo. Purification of the residue by flash chromatography using 25% hexanes in ethyl acetate as the eluent and concentration of the product-rich fractions in vacuo provided ether LXXI. A mixture of LXXI (0.74 g) and HCl (5 mL, 4.0 M in dioxane) in 10 mL anhydrous dioxane was stirred overnight. Collection of the precipitate by vacuum filtration provided LXXII. LXXVII (Example 1) (0.23 g), saturated NaHCO$_3$ (15 mL), dichloromethane (15 mL), phosgene (2.1 mL, 1.93M in toluene) and LXXII (0.32 g) were reacted according to Method B (Scheme I and Example 1). Purification of the residue by flash chromatography using 25% hexanes in ethyl acetate as the eluent, concentration of the product-rich fractions in vacuo, followed by recrystallization from ethyl acetate/methanol provided urea 3, m.p. 205–207° C.

Example 4

1-[5-tert-butyl-2-p-tolyl-2H-pyrazol-3-yl]-3-[4-(2-(morpholin-4-yl)-2-oxoethoxy)naphthalen-1-yl]-urea (4):

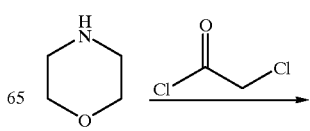

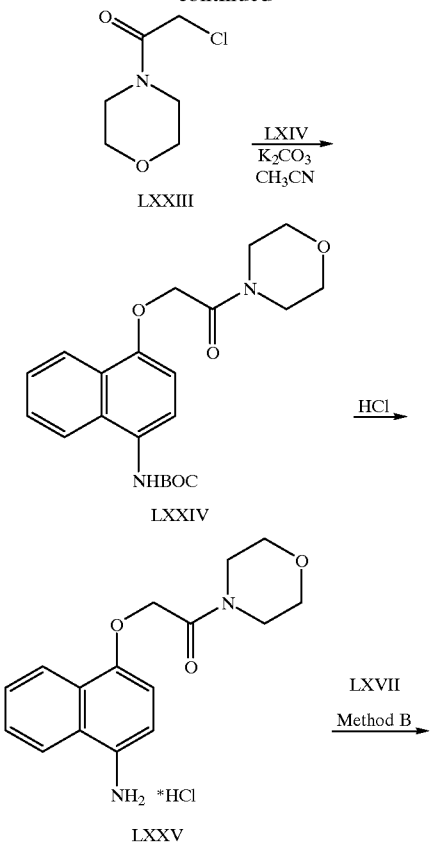

Example 5

1-[5-tert-butyl-2-p-tolyl-2H-pyrazol-3-yl]-3-[4-(2-(1-oxothiomorpholin-4-yl)ethoxy)naphthalen-1-yl]-urea (5):

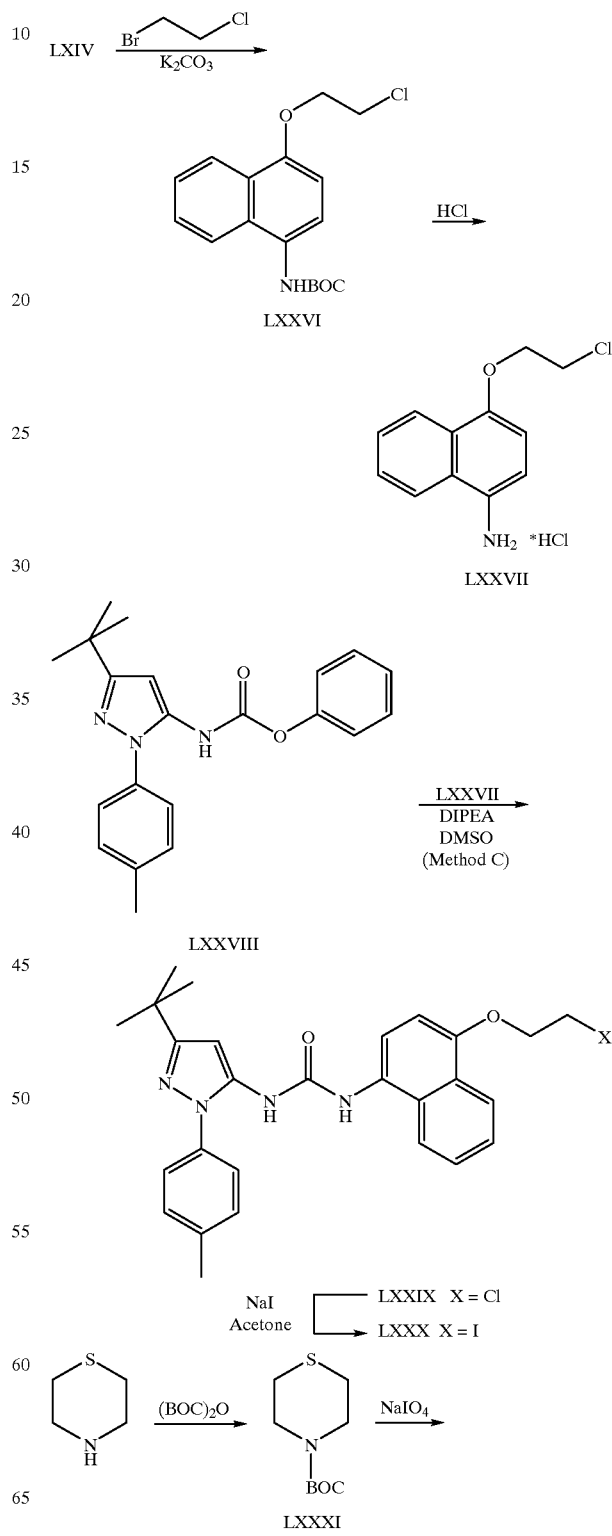

To a solution of morpholine (0.55 mL) in 5 mL of anhydrous ether at 0° C. was added chloroacetyl chloride. Collection of the precipitate by vacuum filtration provided amide LXXIII. A mixture of LXIV (Example 1) (0.44 g), LXXIII (0.30 g), and powered potassium carbonate (0.70 g) in 10 mL acetonitrile was heated to 80° C. for 3.5 hours, cooled to room temperature, and diluted with ethyl acetate and water. The organic layer was washed with water, saturated NaHCO$_3$, brine, dried (MgSO$_4$) and the volatiles removed in vacuo. Purification of the residue by flash chromatography using 20% ethyl acetate in hexanes as the eluent and concentration of the product-rich fractions in vacuo provided ether LXXIV. A mixture of LXXIV (0.26 g) and HCl (0.7 mL, 4.0 M in dioxane) in 4 mL anhydrous dioxane was stirred overnight. Collection of the precipitate by vacuum filtration provided LXXV. LXVII (Example 1), (0.13 g), and LXXV were reacted according to Method B (Scheme I and Example 1). Trituration of the residue in hot methanol/water followed by collection of the solid by vacuum filtration provided urea 4, m.p. 240–241° C.

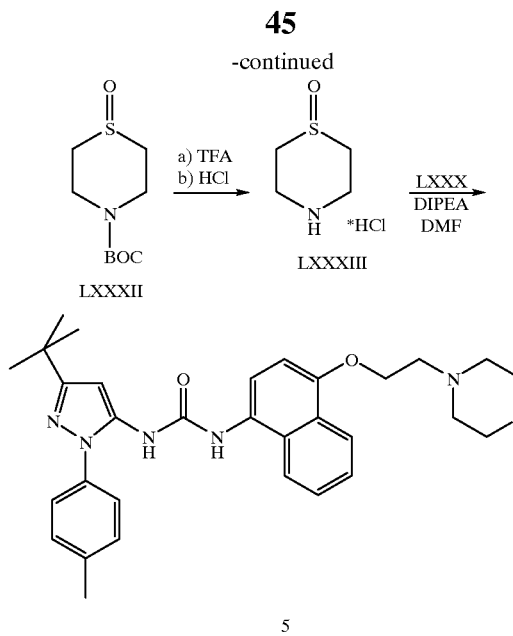
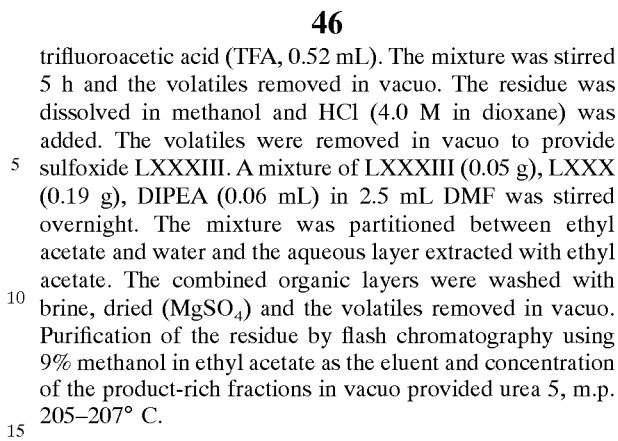

A suspension of LXIV (Example 1) (5.0 g), powdered potassium carbonate (13.3 g) and 1-bromo-2-chloroethane (5.5 g) in 100 mL acetonitrile was heated at 80° C. overnight, cooled to room temperature and partitioned between ethyl acetate and water. The organic layer was washed with brine, dried (MgSO$_4$) and the volatiles removed in vacuo. Purification of the residue by flash chromatography using 25% ethyl acetate in hexanes as the eluent and concentration of the product-rich fractions in vacuo provided ether LXXVI. A mixture of LXVI (2.0 g) and HCl (15 mL, 4.0 M in dioxane) in 10 mL anhydrous dioxane was stirred overnight. Ether was added and the precipitate collected by vacuum filtration to afford LXXVII. As outlined in Method C, (Scheme I) a solution of LXXVII (1.6 g), phenyl carbamate LXXVIII, prepared from LXVII, phenyl chloroformate (1.05 equiv), pyridine (3 equiv.) in THF, (2.3 g) and diisopropylethylamine (3.1 g) in 10 mL anhydrous DMSO was stirred for one hour and diluted with ethyl acetate and water. The organic layer was washed with water, 50% NaHCO$_3$, brine, dried (MgSO$_4$), and the volatiles removed in vacuo. Purification of the residue by flash chromatography using 33% ethyl acetate in hexanes as the eluent, concentration of the product-rich fractions in vacuo, followed by trituration with 33% ethyl acetate in hexanes provided LXXIX. A mixture of LXXIX (1.6 g) and sodium iodide (5.0 g) in 10 mL acetone was heated at reflux for 4 days, cooled to room temperature and diluted with dichloromethane. The organics were washed with water, dried (Na$_2$SO$_4$) and the volatiles removed in vacuo to provide LXXX.

To a solution of thiomorpholine (0.50 g) in 25 mL of dichloromethane was added di-tert-butyldicarbonate. The mixture was stirred for 18 h at room temperature and the volatiles removed in vacuo. Recrystallization of the residue from hexanes provided LXXXI. To a solution of LXXXI (0.40 g) in 8 mL ethanol at 0° C. was added sodium periodate. The mixture was stirred at 0° C. one hour, warmed to room temperature and stirred five days. The mixture was diluted with water and extracted with dichloromethane. The organic layer was washed with brine, dried (Na$_2$SO$_4$) and the volatiles removed in vacuo. Trituration of the residue with hexanes provided sulfoxide LXXXIII. To a solution of LXXXIII (0.15 g) in 5 mL dichloromethane was added trifluoroacetic acid (TFA, 0.52 mL). The mixture was stirred 5 h and the volatiles removed in vacuo. The residue was dissolved in methanol and HCl (4.0 M in dioxane) was added. The volatiles were removed in vacuo to provide sulfoxide LXXXIII. A mixture of LXXXIII (0.05 g), LXXX (0.19 g), DIPEA (0.06 mL) in 2.5 mL DMF was stirred overnight. The mixture was partitioned between ethyl acetate and water and the aqueous layer extracted with ethyl acetate. The combined organic layers were washed with brine, dried (MgSO$_4$) and the volatiles removed in vacuo. Purification of the residue by flash chromatography using 9% methanol in ethyl acetate as the eluent and concentration of the product-rich fractions in vacuo provided urea 5, m.p. 205–207° C.

Example 6

1-[5-tert-butyl-2-p-tolyl-2H-pyrazol-3-yl]-3-[4-(2-pyridin-4-yl-ethenyl)naphthalen-1-yl]-urea (6):

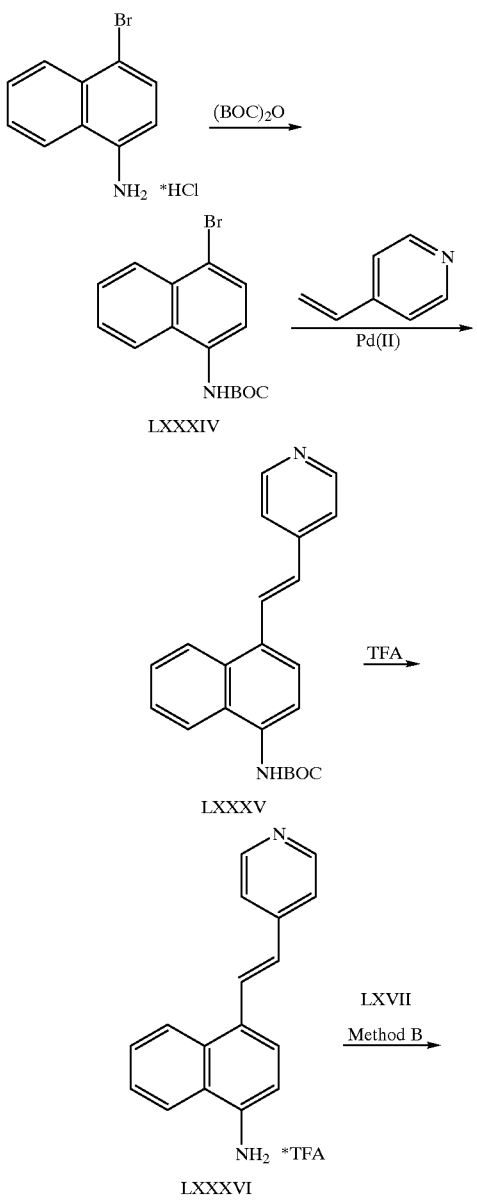

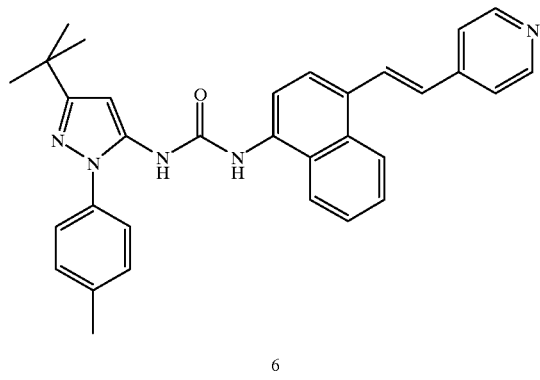

6

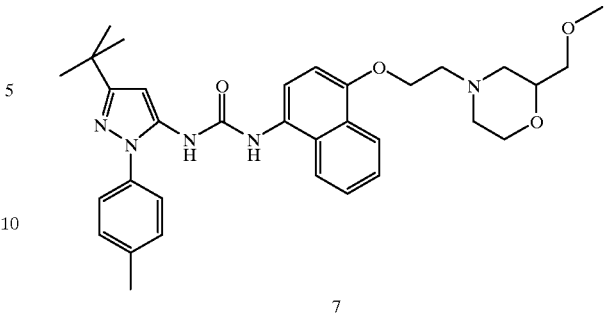

7

A mixture of 4-bromoaminonaphthalene (5.0 g) and di-tert-butyldicarbonate (5.9 g) in 100 mL toluene was heated at 70° C. for 15 hours, cooled to room temperature and the volatiles removed in vacuo. The residue was dissolved in ethyl acetate, washed with 0.1M HCl and brine, dried (MgSO₄) and the volatiles removed in vacuo. Recrystallization of the residue from hot petroleum ether provided LXXXIV. 4-Vinylpyridine (0.86 mL) was added to a suspension of LXXXIV (2.0 g) in 5 mL of triethylamine, followed by palladium (II) acetate (0.014 g) and tri-ortho-tolylphosphine (0.038 g). The mixture was heated at 110° C. for four hours, cooled to room temperature, diluted with water and ethyl acetate. The organic layer was washed with brine, dried (MgSO₄) and the volatiles removed in vacuo. Purification of the residue by flash chromatography using 50% ethyl acetate in hexanes as the eluent and concentration of the product-rich fractions in vacuo provided naphthalene LXXXV. A solution of LXXXV (0.34 g) in 10 mL TFA was stirred one hour and the volatiles removed in vacuo to provided LXXXVI. LXXXVI and LXVII (Example 1) were reacted according to Method B to provide 6, m.p. 203° C. (dec).

A mixture of LXXXVII (prepared by the method of Y. Jinbo et al; *J. Med. Chem.*, 1994, 37, 2791) (0.044 g), LXXX (see Example 5) (0.15 g) and DIPEA (0.068 g) was stirred overnight, diluted with ether and water. The organic layer was washed with brine, dried (MgSO₄) and the volatiles removed in vacuo. Purification of the residue by flash chromatography using a gradient of 1–4% methanol in ethyl acetate as the eluent and concentration of the product-rich fractions in vacuo provided 7, m.p. 85–90° C.

Example 8

1-[5-tert-butyl-2-p-tolyl-2H-pyrazol-3-yl]-3-[4-(2-morpholin-4-yl-ethoxy)naphthalen-1-yl]-urea (8):

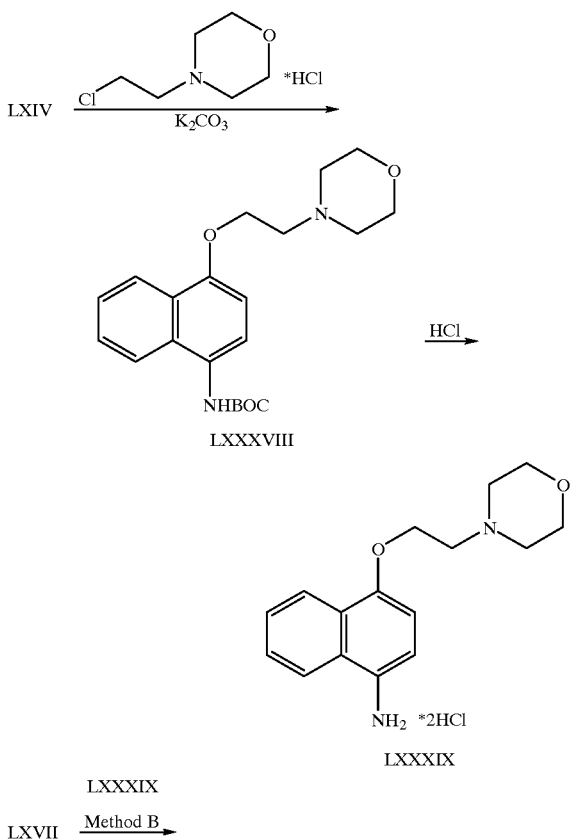

Example 7

1-[5-tert-butyl-2-p-tolyl-2H-pyrazol-3-yl]-3-[4-(2-(2-(methoxymethyl)morpholin-4-yl)ethoxy) naphthalen-1-yl]-urea (7):

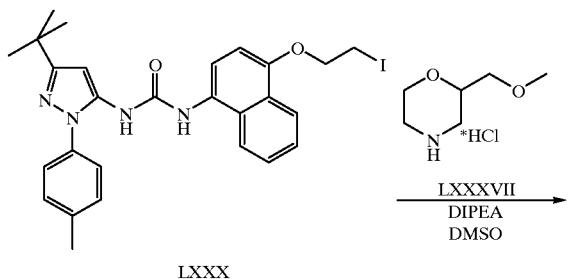

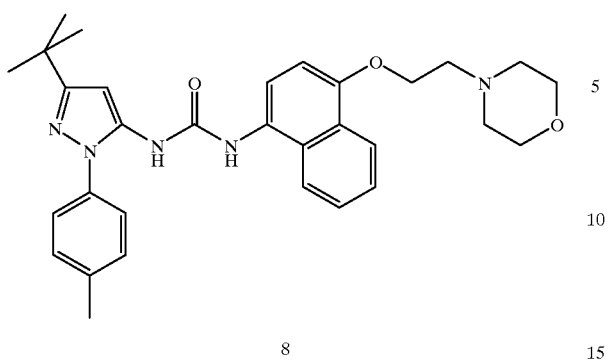

8

A mixture of LXIV (Example 1) (0.464 g), 4-(2-chloroethyl)morpholine hydrochloride (0.3435 g) and powdered potassium carbonate (0.93 g) was heated in acetonitrile (15 mL) at 80° C. for 3 hours, cooled to room temperature and diluted with ethyl acetate and water. The organic layer was washed with water, brine, dried (MgSO$_4$) and the volatile removed in vacuo. Purification of the residue by flash chromatography using 12% hexanes in ethyl acetate as the eluent and concentration in vacuo of the product-rich fractions afforded LXXXVIII. A solution of LXXXVIII (0.511 g) and HCl (1 mL of a 4M dioxane solution) in 5 mL dioxane was stirred at room temperature 20 hours. Removal of the volatiles in vacuo provided the product LXXXIX, which was reacted with LXVII (Example 1) according to Method B to provide 8, m.p. 142–143° C.

Example 9

1-[5-tert-butyl-2-(2-methylpyridin-5-yl)-2H-pyrazol-3-yl]-3-[4-(2-morpholin-4-yl-ethoxy)naphthalen-1-yl]-urea (9):

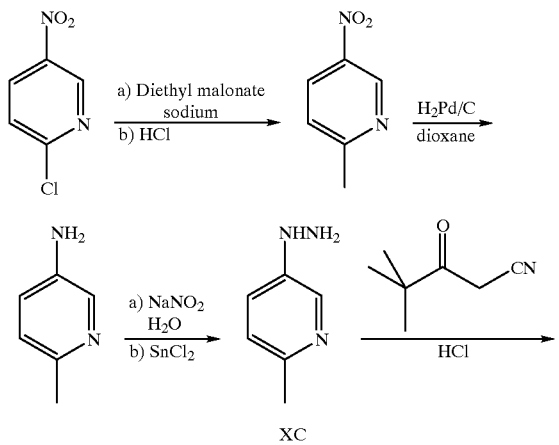

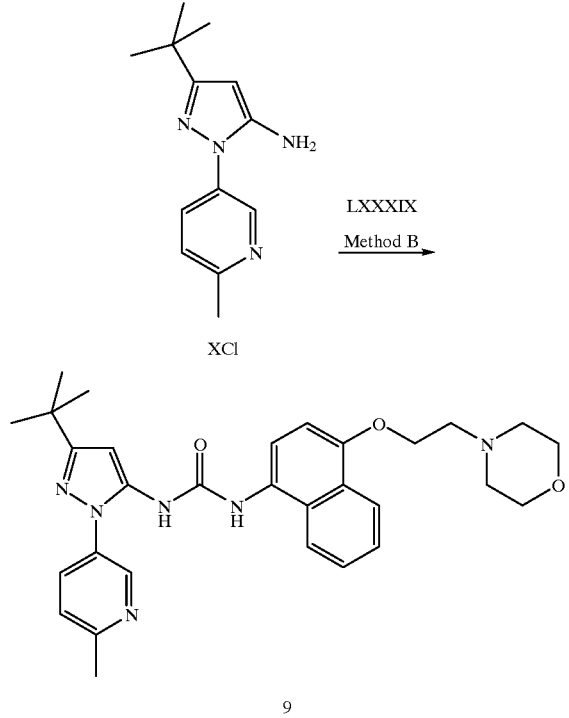

9

A slurry of diethyl malonate (42 mL) and sodium (4.71 g) was warmed slowly to 90° C. and stirred at 90° C. for 2 hours and 120° C. for 30 min. before being cooled to room temperature. Toluene (200 mL) and 2-chloro-5-nitropyridine (25.0 g) were added and the mixture was heated at 110° C. for 1.5 hours and ambient temperature for 17 h. After removal of the volatiles in vacuo, 6 N HCl (200 mL) was added and the mixture heated to reflux for 4 h and cooled to room temperature. The solution was neutralized with solid sodium carbonate, extracted with ethyl acetate (6×100 mL), dried over solid magnesium sulfate, and concentrated to a dark solid. This material was purified by flash chromatography using 20% ethyl acetate in petroleum ether as the eluent. Concentration in vacuo of the product-rich fraction afforded 2-methyl-5-nitropyridine. A mixture of 2-methyl-5-nitropyridine (13.0 g) and 10% Pd on activated carbon (0.1 g) in 1,4-dioxane (150 mL) was hydrogenated at 50 psi for 24 hours and filtered over celite. Removal of the volatiles in vacuo provided 2-methyl-5-aminopyridine. A solution of this compound (9.90 g) was dissolved in 6 N HCl (100 mL), cooled to 0° C., and vigorously stirred throughout the procedure. Sodium nitrite (6.32 g) in water (50 mL) was added. After 30 min, tin (II) chloride dihydrate (52.0 g) in 6 N HCl (100 mL) was added and the reaction slurry was stirred at 0° C. for 3 hours. The pH was adjusted to pH 14 with 40% aqueous potassium hydroxide solution and extracted with ethyl acetate. The combined organic extracts were dried (MgSO$_4$) and removal of the volatiles in vacuo provided hydrazine XC. A solution of XC (8.0 g) and 4,4-dimethyl-3-oxopentanenitrile (10.0 g) in ethanol (200 mL) and 6 N HCl (6 mL) was refluxed for 17 hours and cooled to room temperature. Solid sodium hydrogen carbonate was added to neutralize the solution. The slurry was filtered and removal of the volatiles in vacuo provided a residue which was purified by column chromatography using ethyl acetate as the eluent. Concentration in vacuo of the product-rich fractions afforded XCI, which was reacted with LXXXIX (Example 8) according to Method B to provide 9, m.p. 121–123° C.

Example 10

1-[5-tert-butyl-2-(2-methylpyridin-5-yl)-2H-pyrazol-3-yl]-3-[4-(2-pyridin-4-yl-ethoxy)naphthalen-1-yl]-urea (10)

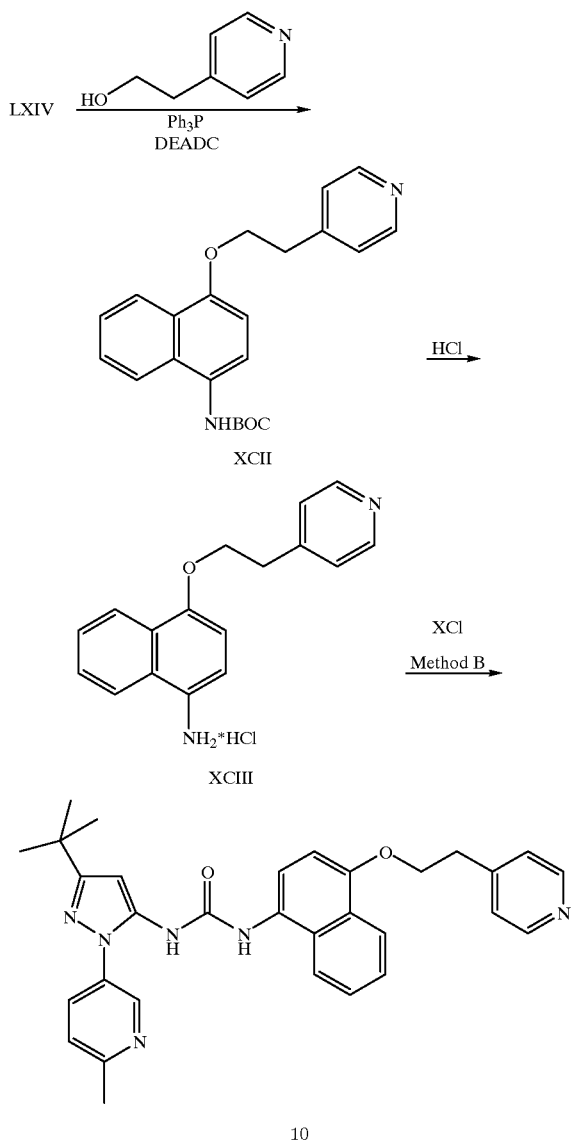

To a solution of LXIV (Example 1) (0.962 g), 2-(pyridin-4-yl)ethanol (1.4 g) and triphenylphosphine (2.90 g) in THF (25 mL) was added dropwise DEADC (1.8 mL). The mixture was stirred overnight and the volatiles removed in vacuo. Purification of the residue with flash chromatography using ethyl acetate as the eluent and concentration in vacuo of the product-rich fractions provided XCII. To a solution of XCII (1.4 g) in dioxane (15 mL) was added HCl (10 mL of a 4M dioxane solution). The solution was stirred overnight and product XCIII was filtered and dried. This was reacted with XCI (Example 9) according to Method B to provide 10, m.p. 189–190° C.

Example 11

1-[5-(1-methylcyclohex-1-yl)-2-phenyl-2H-pyrazol-3-yl]-3-[4-(2-morpholin-4-yl-ethoxy)naphthalen-1-yl]-urea (11):

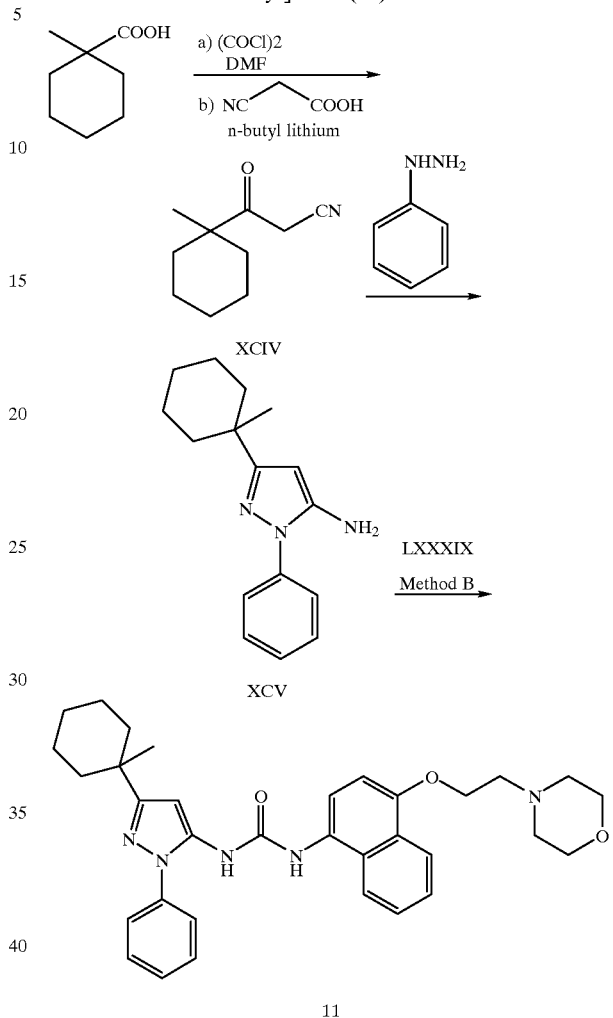

To a solution of cyclohexane-1-methyl-1-carboxylic acid (1.31 g) in 5 mL methylene chloride was added oxalyl chloride solution (5.5 mL of a 2.0 M methylene chloride solution) and 1 drop of anhydrous DMF. The mixture was refluxed for 3 hours under inert atmosphere and cooled to room temperature. Cyanoacetic acid (1.57 g) in ethyl acetate was dried (MgSO$_4$) and the volatiles removed in vacuo. The residue and 2,2-bipyridine (~10 mg) in anhydrous THF (70 mL) was cooled to −70° C. and treated with n-BuLi (2.5 M in Hexanes) slowly, while allowing the reaction mixture to reach 0° C. When the red color persists at 0° C. (ie. after 15.0 mL of n-BuLi solution), the solution was recooled to −70° C. and the acid chloride solution from above (9.21 mmol) was added via syringe in one portion. The mixture was warmed to room temperature, stirred 0.5 hours, poured onto 1 N aq. HCl (200 mL) and extracted with chloroform (3×100 mL). The combined organic layers were washed with saturated aqueous NaHCO$_3$, brine and dried (MgSO$_4$). Removal of volatiles in vacuo provided a residue which was purified by column chromatography using hexanes and ethyl acetate as the eluent. Concentration in vacuo of the product-rich fractions provided XCIV. A solution of XCIV (0.80 g) and phenylhydrazine (0.48 mL) in toluene (5 mL) was heated with azeotropic removal of water overnight and the volatiles removed in vacuo. Purification of the residue with flash chromatography using ethyl acetate and hexanes as the eluent and concentration in vacuo of the product-rich frac-

Example 12

1-[5-tert-butyl-2-p-tolyl-2H-pyrazol-3-yl]-3-[4-(pyridin-4-yl-methylamino)naphthalen-1-yl]-urea (12):

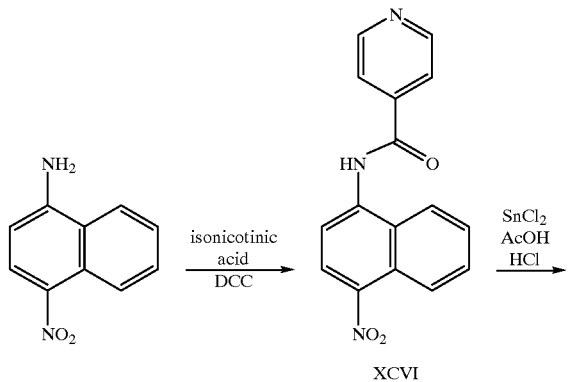

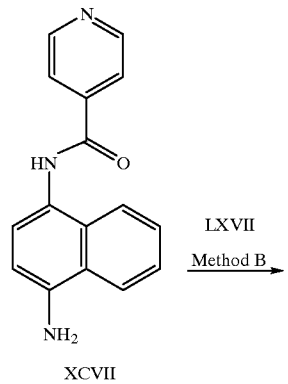

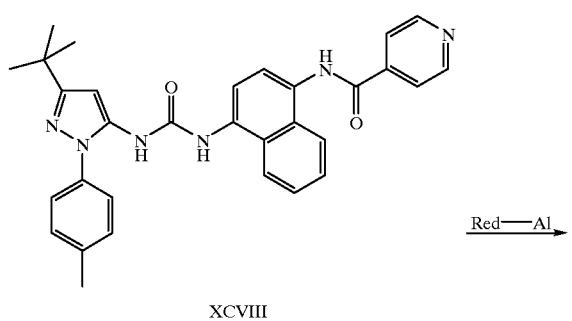

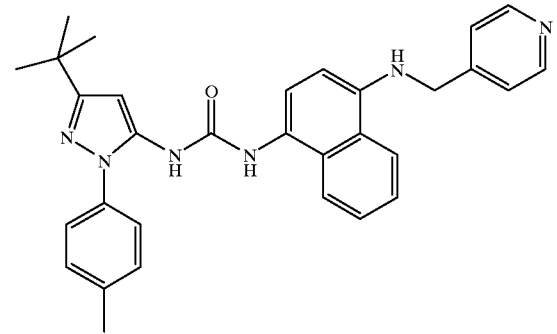

12

Isonicotinic acid (1.13 g) and DCC (2.5 g) were mixed together in methylene chloride (80 mL) under an inert atmosphere and at room temperature. After 30 min 4-nitro-1-naphthylamine (1.70 g) was added to this suspension as well as a catalytic amount of DMAP (~50 mg). After 2 days the suspension was filtered through Celite, the volatiles removed in vacuo and the residue purified by column chromatography to afford XCVI. A mixture of XCVI (0.299 g) in acetic acid (6 mL) was treated at room temperature with a solution of tin chloride (1.55 g) in 6 mL of concentrated HCl. After stirring for 1.5 hours, the mixture was poured slowly into 200 mL 15% aqueous NaOH solution and extracted with ethyl acetate (3×100 mL). Drying (MgSO$_4$), removal of volatiles in vacuo and purification of the residue by column chromatography using 5% methanol in ethyl acetate as the eluent afforded XCVII, which was reacted with LXVII (Example 1) according to Method B to provide XCVIII. To a suspension of XCVIII (0.101 g) in anhydrous THF (7 mL) at room temperature was added dropwise Red-Al (65% w/w solution in toluene; 0.27 mL) under an inert atmosphere. The mixture was then refluxed for 1 h (dark red color), cooled and methanol was added dropwise until no more evolution of H$_2$ was detected. Removal of most of the solvent in vacuo provided a residue which was purified by column chromatography using hexanes, 50% ethyl acetate in hexanes and finally ethyl acetate as the eluents. Concentration of the product-rich fractions in vacuo furnished solid 12, m.p. 174–177° C.

Example 13

1-[5-tert-butyl-2-(3-(2-morpholin-4-yl-ethyl)phenyl)-2H-pyrazol-3-yl]-3-[4-(2-morpholin-4-yl-ethoxy)naphthalen-1-yl]-urea (13):

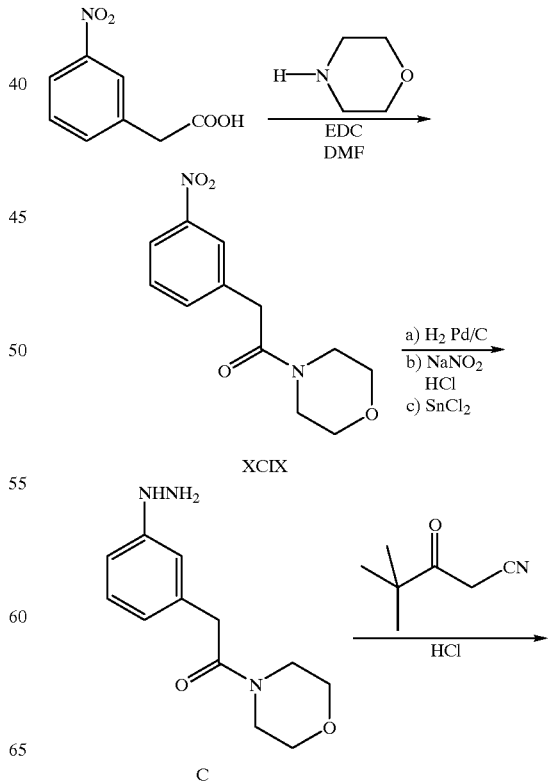

-continued

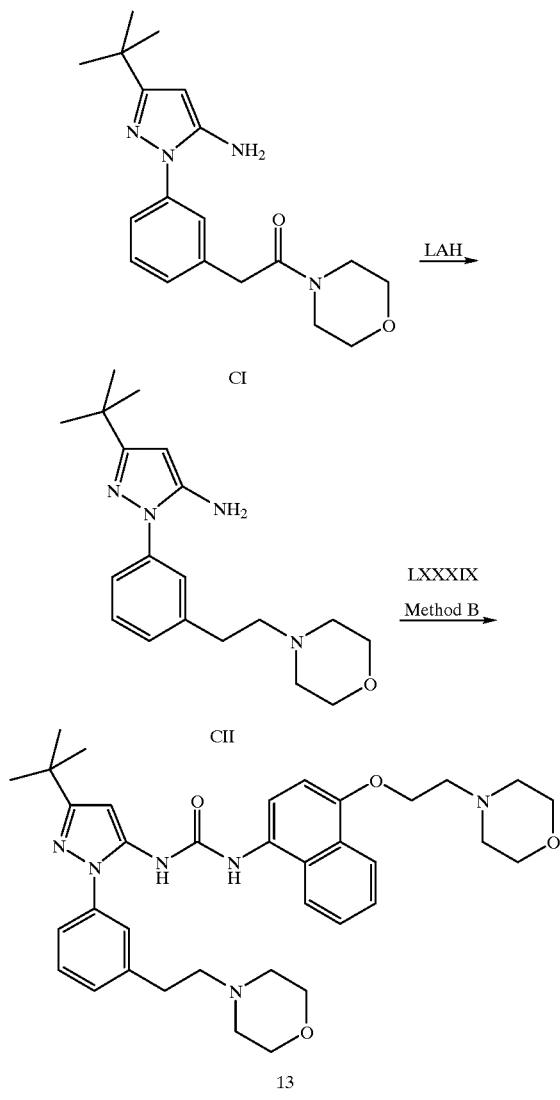

A mixture of 3-nitrophenylacetic acid (5.02 g), morpholine (4.83 mL) and EDC (10.62 g) in 80 mL DMF at room temperature was stirred for 6 hours and diluted with water and extracted with ethyl acetate. The combined organic extracts were washed with water and brine and dried (MgSO$_4$). Removal of the volatiles in vacuo provided XCIX. A mixture of XCIX (6.7 g) and 10% Pd on carbon (0.1 g) in ethyl acetate (100 mL) was hydrogenated at 45 psi for 15 hours and filtered over celite. Removal of the volatiles in vacuo furnished an amine (5.7 g) which was dissolved in 6 N HCl (40 mL), cooled to 0° C., and vigorously stirred. Sodium nitrile (2.11 g) in water (5 mL) was added in dropwise fashion. After 30 min, tin (II) chloride dihydrate (52.0 g) in 6 N HCl (100 mL) was added via addition funnel and the reaction slurry was stirred at 0° C. for 3 hours. The pH was adjusted to 14 with 40% aqueous sodium hydroxide solution and the solution extracted with ethyl acetate. The organic layers were dried (MgSO$_4$). Removal of the volatiles in vacuo provided C. A solution of C (2 g) and 4,4-dimethyl-3-oxopentanenitrile (1.1 g) in ethanol (80 mL) containing 6 N HCl (2 mL) was refluxed for 17 hours, cooled to room temperature and the pH was adjusted to 14 with 40% aqueous sodium hydroxide solution. The mixture was extracted with ethyl acetate and the combined organic extracts were dried (MgSO$_4$). Removal of the volatile in vacuo provided CI. To a solution of CI (150 mg) in dry THF (10 mL) at 0° C. was added dropwise a solution of LAH in ether (2.13 mL of a 1M solution). The mixture was slowly warmed to 60° C. stirred for 5 hours, cooled to room temperature and stirred 16 hours. The reaction was quenched with the addition of 10% aqueous NaOH solution until a neutral pH was achieved. The mixture was extracted with ethyl acetate and the combined organic extracts were dried (MgSO$_4$). Removal of the volatile in vacuo provided a residue which was purified by column chromatography using ethyl acetate as the eluent. Concentration of the product-rich fractions in vacuo furnished CH, which was reached with LXXXIX (Example 8) according to Method E to provide 13, as a oil.

Example 14

1-[5-tert-butyl-2-p-tolyl-2H-pyrazol-3-yl]-3-[4-(3-morpholin-4-yl-propyl)naphthalen-1-yl]-urea (14):

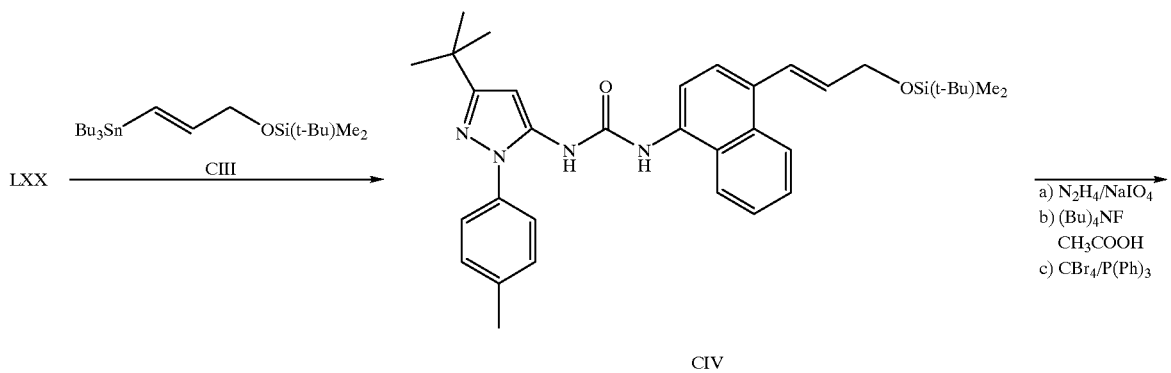

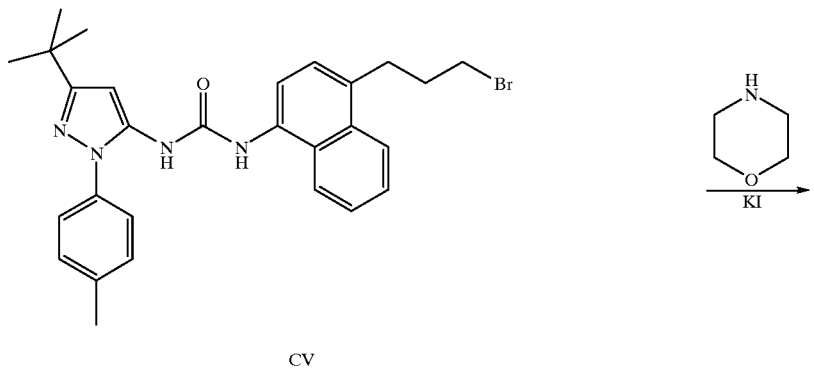

CV

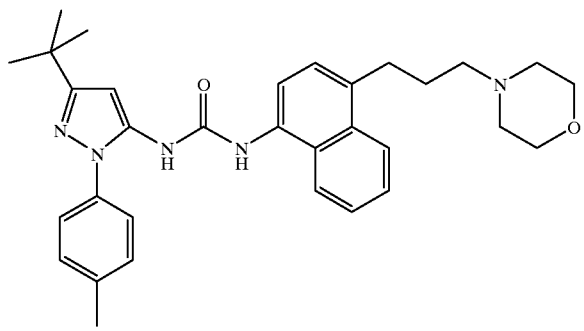

14

A mixture of LXX (Example 2) (3.0 g), CIII (prepared by the procedure of J. W. Labadic et al; 1983, J. Org. Chem. 48, 4634) (3.0 g) and tetrakistriphenylphosphinepalladium (0.15 g) in 18 mL toluene was heated to 100° C. for 30 min. Another 0.050 g of catalyst was added. The mixture was heated three hours, cooled to room temperature, diluted with ether and washed with 5% NH$_4$OH, water, brine, dried (MgSO$_4$) and the volatiles removed in vacuo. Purification of the residue by flash chromatography using 1% methanol in dichloromethane as the eluent and concentration of the product-rich fractions in vacuo provided CIV. To CIV (2.2 g), and hydrazine (4.9 g) in 50 mL ethanol and 10 mL THF at 0° C. was added dropwise a solution of sodium periodate (8.1 g) in 15 mL water. The mixture was warmed to room temperature, stirred six hours, heated to 40° C. for two hours and diluted with dichloromethane, washed with 1N sodium hydroxide, water, brine and dried (MgSO$_4$). Removal of the volatiles in vacuo provided the saturated olefin. A mixture of this alkane (2.1 g) and tetrabutylammonium fluoride (14.4 mL, 1M in THF) and acetic acid (1.1 g) was stirred overnight, diluted with ethyl acetate and washed with water, brine, and dried (MgSO$_4$). Removal of the volatiles in vacuo, purification of the residue by flash chromatography suing 33% hexanes in ethyl acetate as the eluent and concentration of the product-rich fractions in vacuo provided the alcohol. To a solution of this alcohol (0.60 g) in acetonitrile at 0° C. was added triphenylphosphine (0.52 g) then carbon tetrabromide (0.65 g). The mixture was stirred at room temperature for two days and the volatiles removed in vacuo.

Purification of the residue by flash chromatography using 33% ethyl acetate in hexanes as the eluent and concentration of the product-rich fractions in vacuo provided CV. A mixture of CV (0.23 g), morpholine (0.039 g), KI (0.073 g) and DIPEA (0.1 mL) in DMF (3 mL) was stirred 6 hours at room temperature and diluted with ether and water. The organic layer was washed with brine and dried (MgSO$_4$). Removal of the volatiles in vacuo provided a residue which was purified by flash chromatography using ethyl acetate as the eluent. Concentration in vacuo of the product-rich fractions provided 14 which was recyrstallized from hexanes and ethyl acetate, m.p. 147–149° C.

Table 1 illustrates additional compounds of the invention, which were prepared by methods analogous to those described above.

TABLE 1

Ar₁ = pyrazole with R₁ at 3-position and R₃ on N; Ar₂ = naphthyl

General structure: Ar₁-NH-C(O)-NH-Ar₂-L-Q

| Ex. No. | R₁ | R₃ | Q-L- | m |
|---|---|---|---|---|
| 15 | tert-butyl | 2-Cl-pyridin-5-yl | 2-(morpholin-4-yl)ethoxy | 123-17 |
| 16 | tert-butyl | 4-methyl-phenyl | 2-(imidazol-1-yl)ethoxy | 201-2 |
| 17 | tert-butyl | 2-methoxy-pyridin-5-yl | 2-(morpholin-4-yl)ethoxy | 108-1 |
| 18 | tert-butyl | pyridin-3-yl | 2-(morpholin-4-yl)ethoxy | 191-1 |
| 19 | tert-butyl | 4-Cl-phenyl | 2-(morpholin-4-yl)ethoxy | 116-1 |
| 20 | tert-butyl | 4-methyl-phenyl | pyridin-3-ylmethylamino | 137-1 |
| 21 | tert-butyl | 4-methyl-phenyl | morpholin-4-yl-methyl | 17 |
| 22 | tert-butyl | 4-methyl-phenyl | 2-(pyridin-4-yl)ethoxy | 187- |
| 23 | tert-butyl | 4-methyl-phenyl | 3-(pyridin-3-yl)-n-propoxy | 162- |
| 24 | tert-butyl | 4-methyl-phenyl | morpholine-4-carbonyloxyethoxy | 176- |
| 25 | tert-butyl | 4-methyl-phenyl | 2-(morpholin-4-yl)ethoxy (Ar₂ = 3-methylnapth-1-yl) | 176- |
| 26 | tert-butyl | 4-methyl-phenyl | 2-(pyridin-4-yl)ethyl | 117- |
| 27 | tert-butyl | methyl | 2-(morpholin-4-yl)ethoxy | 201- |
| 28 | tert-butyl | 4-methyl-phenyl | 2-(thiomorpholin-4-yl)ethoxy | 122- |
| 29 | tert-butyl | 4-methyl-phenyl | 2-(piperazin-1-yl)ethoxy | |
| 30 | tert-butyl | 4-methyl-phenyl | 2-(morpholin-4-yl)-n-propoxy | 110 |
| 31 | tert-butyl | 4-methyl-phenyl | 2-(4-tetrahydropyran-4-yl)ethoxy | 174 |
| 32 | tert-butyl | 4-methyl-phenyl | 3-(morpholin-4-yl)propyn-1-yl | 120 |
| 33 | tert-butyl | 4-methyl-phenyl | 3-(piperidin-1-yl)propyn-1-yl | 109 |
| 34 | tert-butyl | 4-methyl-phenyl | 4-[4-(tetrahydropyran-2-yloxy)but-1-ynyl] | 180 |
| 35 | tert-butyl | 4-methyl-phenyl | 2-(3,4-dimethoxyphenyl)ethoxy | 182 |
| 36 | tert-butyl | 4-methyl-phenyl | (pyridine-4-carbonyl)amino | > |
| 37 | i-Pr | phenyl | 2-(morpholin-4-yl)ethyl | 17 |
| 38 | CF₃CH₂ | 4-methyl-phenyl | 2-(morpholin-4-yl)ethyl | 17 |
| 39 | 3-tetrahydro-pyranyl | phenyl | 2-(morpholin-4-yl)ethyl | 15 |
| 40 | cyclohexyl | phenyl | 2-(morpholin-4-yl)ethyl | 19 |
| 41 | tert-butyl | n-butyl | 2-(morpholin-4-yl)ethyl | 8 |
| 42 | tert-butyl | benzyl | 2-(morpholin-4-yl)ethyl | 1 |
| 43 | tert-butyl | 4-methyl-3-morpholin-4-yl-methylphenyl | 2-(morpholin-4-yl)ethyl | oil |
| 44 | tert-butyl | 4-methyl-3-C(O)NH₂-phenyl | 2-(morpholin-4-yl)ethyl | oil |
| 45 | tert-butyl | 4-methyl-3-(dimethyl)NCH₂-phenyl | 2-(morpholin-4-yl)ethyl | oil |
| 46 | tert-butyl | 4-methyl-phenyl | pyridin-4-yl-oxy | |
| 47 | 1-methyl-cycloprop-1-yl | 4-methyl-phenyl | 2-(morpholin-4-yl)ethoxy | 146 |
| 48 | tert-butyl | 4-methyl-phenyl | 2-(morpholin-4-yl)ethoxy Ar₂ = 5, 6, 7, 8-tetrahydronaphthalene | 99- |
| 49 | tert-butyl | 4-methyl-phenyl | 2-(trans-2,6-dimethyl-morpholin-4-yl)ethoxy | 137- |
| 50 | tert-butyl | 4-methyl-phenyl | 2-(cis-2,6-dimethyl-morpholin-4-yl)ethoxy | 153- |
| 51 | tert-butyl | 4-methyl-phenyl | 2-(2-methoxymethyl-morpholin-4-yl)ethoxy | 85- |
| 52 | tert-butyl | 4-methyl-phenyl | 2-(1-oxo-thiomorpholin-4-yl)ethoxy | 205 |
| 53 | tert-butyl | 4-methyl-phenyl | 2-(1-oxo-thiazolidin-3-yl)ethoxy | 193 |
| 54 | tert-butyl | 4-methyl-phenyl | 5-methylamino-5-oxo-butyloxy | 117 |

TABLE 1-continued

[Structure: Ar1-NH-C(=O)-NH-Ar2-L-Q]

Ar1 = pyrazole with R1 at 3-position and R3 on N1

Ar2 = naphthyl (1,4-disubstituted)

| Ex. No. | R1 | R3 | Q-L- | m |
|---|---|---|---|---|
| 55 | tert-butyl | 4-methyl-phenyl | 5-amino-5-oxo-butyloxy | fo |
| 56 | tert-butyl | 4-methyl-phenyl | 5-(morpholin-4-yl)-5-oxo-butyloxy | fo |
| 57 | tert-butyl | 2-methyl-pyridin-5-yl | pyridin-4-yl-thio | |

ASSESSMENT OF BIOLOGICAL PROPERTIES
Inhibition of TNF Production in THF Cells The inhibition of cytokine production can be observed by measuring inhibition of TNFα in lipopolysaccharide stimulated THP cells. All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THF.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min., 37° C., 5% $CO_2$ prior to stimulation with lipopolysaccharide (LPS; 1 μg/ml final; Siga L-2630, from *E. coli* serotype 0111.B4; stored at 1 mg/ml stock in endotoxin screened distilled $H_2O$ at −80° C.). Blanks (unstimulated) received $H_2O$ vehicle; final incubation volume was 250 μl. Overnight incubation (18–24 hr) proceeded as described above. Assay was terminated by centrifuging plates 5 min, room temperature, 1600 rpm (400 x g); supernatants were transferred to clean 96 well plates and stored −80° C. until analyzed for human TNFα by a commercially available ELISA kit (Biosource #KHC3015, Camarilo, Calif.). Date was analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Representative compounds from the synthetic examples above and Table 1 were evaluated and all had $IC_{50} < 10$ μM in this assay.

By similar methods using peripheral blood monocytic cells, appropriate stimuli, and commercially available ELISA kits for a particular cytokine, inhibition of IL-1β, GM-CSF, IL-6 and IL-8 was demonstrated by representatives from the synthetic examples and Table 1.

What is claimed is:

1. A method of treating a cytokine mediated disease or condition chosen from: actuate and chronic pain, contact dermatitis, atherosclerosis, glomerulonephritis, reperfusion injury, bone resorption diseases, asthma, stroke, myocardial infarction, thermal injury, adult respiratory distress syndrome (ARDS), multiple organ injury secondary to trauma, dermatoses with actuate inflammatory components, acute purulent meningitis, necrotizing entrerocolities, syndromes associated with hemodialysis, septic shock, leukopherisis and granuloctye transfusion, said method comprising administering to a patient in need of such treatment a therapeutically effective amount of a compound of the formula (I):

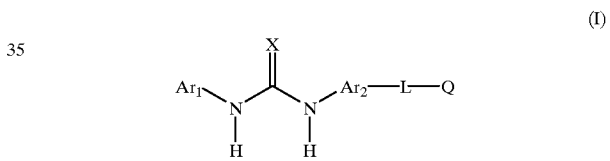

(I)

wherein
- Ar1 is pyrazole optionally substituted by one or more $R_1$, $R_2$ or $R_3$;
- Ar2 is: phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three $R_2$ groups;
- L is a $C_{1-10}$ saturated or unsaturated branch or unbranched carbon chain;
- wherein one or more methylene groups are optionally independently replaced by O, N or S; and
- wherein said linking group is optionally substituted with 0–2 oxo groups and one or more $C_{1-4}$ branched or unbranched alkyl which may be substituted by one or more halogen atoms;
- Q is selected from the group consisting of:
  a) pyridine, pyrimidine, pyridazine, imidazole, benzimidazole, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino; $C_{1-4}$ alkyl-S(O)$_m$ and phenylamino wherein the phenyl ring is optionally substituted with one to two groups selected from the group consisting of halogen, $C_{1-6}$ alkyl and $C_{1-6}$ alkoxy;

b) morpholine, thiomorpholine, thiomorpholine sulfoxide, thiomorpholine sulfone, piperidine, piperidinone and tetrahydropyrimidone which are optionally substituted with one to three groups selected from the group consisting of $C_{1-6}$ alkyl, $C_{1-6}$ alkoxy, hydroxy, mono- or di-($C_{1-3}$ alkyl)amino-$C_{13}$ alkyl, phenylamino-$C_{1-3}$ alkyl and $C_{1-3}$ alkoxy-$C_{1-3}$ alkyl;

$R_1$ is selected from the group consisting of a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocyclic selected from the group hereinabove described being substituted with 0 to 5 groups selected from the halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, $NH_2C(O)$ and di($C_{1-3}$) alkylaminocarbonyl;

b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$alkyl groups, or an analog of such cycloalkyl group wherein one to three ring methylene groups are replaced by groups independently selected from O, S, CHOH, <C=O, <C=S and NH, c) $C_{3-10}$ branched alkenyl which may optionally be partially or fully halogenated, and which is optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkyloxy which is optionally partially or fully halogenated, $NH_2CO(O)$, mono- or di($C_{1-3}$)alkylaminocarbonyl;

d) $C_{5-7}$ cycloalkenyl selected from the group consisting of cyclopentanyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

e) cyano; and, f) methoxycarbonyl, ethoxycarbonyl and propoxycarbonyl;

$R_2$ is selected from the group consisting of: a $C_{1-4}$ branched or unbranched alkyl which may optionally be partially or fully halogenated, acetyl, aroyl, $C_{1-4}$ branched or unbranched alkoxy, which may optionally be partially or fully halogenated, halogen, methoxycarbonyl and phenylsulfonyl;

$R_5$ is selected from the group consisting of:

a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazlyl, isothiazolyl, quinolinyl, isoquinolinyl, indolyl, benzimidazoly, benzofuranyl, benzoxazolyl, benzisoxazolyl, benzpyrazolyl, benzothiofuranyl, cinnolinyl, pterindinyl, pthalazinyl, naphthypyridinyl, quinoxalinyl, quinazolinyl, purinyl and indazolyl, wherein such phenyl, naphthyl or heterocyclic group is optionally substituted with one to five groups selected from the group consisting of a $C_{1-6}$ branched or unbranched alkyl, phenyl, naphthyl, heterocycle selected from the group hereinabove described, $C_{1-4}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$alkyl, naphthyl $C_{1-5}$ alkyl, halo, hydroxy, cyano, $C_{1-5}$ alkyloxy which may optionally be partially or fully halogenated, phenyloxy, naphthyloxy, heteraryloxy wherein the heterocyclic moiety is selected from the group hereinabove described, nitro, amino, mono- or Di-($C_{1-3}$)alkylamino, phenylamino, naphthylamino, heterocyclclamino wherein the heterocyclyl moiety is selected from the group hereinabove described, $NH_2C(O)$, a mono- or di-($C_{1-3}$)alkyl aminocarbonyl, $C_{1-5}$ alkyl-C(O)-$C_{1-4}$alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$-$C_{1-5}$alkyl, $R_5$-$C_{1-5}$alkoxy, $R_6$-C(O)-$C_{1-5}$ alkyl and $R_7$-$C_{1-5}$ alkyl ($R_8$)N;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopytimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cycloheanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanolmidazole, cyclopentanothiophene and cyclohexanothiophene; wherein the fused aryl or fused heterocyclyl ring is substituted win 0 to 3 groups independently selected from phenyl, naphthyl and heterocycl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halo, cyano, $C_{1-2}$ alkyloxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino; heterocyclylamino wherein the heterocyclyl moiety is selected from the group hereinabove described, $NH_2C$ (O), a mono- or di-($C_{1-3}$)alkyl aminocarbonyl, $C_{1-4}$ alkyl-OC(O), $C_{1-5}$ alkyl-C(O)-$C_{1-4}$ branched or unbranched alkyl, an amino-$C_{1-5}$ alkyl, mono- or di-($C_{1-3}$)alkylamino-$C_{1-5}$ alkyl, $R_9$–$C_{1-5}$ alkyl, $R_{10}$-$C_{1-5}$ alkoxy, $R_{11}$—C(O)—$C_{1-5}$ alkyl and $R_{12}$–$C_{1-5}$ alkyl ($R_{13}$)N;

c) cycloalkyl selected from the group consisting of cyclopentanyl, cyclohexanyl, cycloheptanyl, bicyclopentanyl, bicyclohexanyl and bicycloheptanyl, which the cycloalkyl may optionally be partially or fully halogenated and which may optionally be substituted with one to three $C_{1-3}$ alkyl groups;

d) $C_{5-7}$cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-5}$ alkyl groups; and e) acetyl, aroyl, alkoxycarbonylalkyl or phenylsulfonyl;

f) $C_{1-6}$ branched or unbranched alkyl which may optionally be partially or fully halogenated;

wherein or $R_1$ and $R_2$ taken together may optionally form a fused phenyl or pyridinyl ring;

each $R_8$, $R_{13}$ is independently selected from the group consisting of hydrogen and $C_{1-4}$ branched or unbranched alkyl which may optionally be partially or fully halogenated;

each $R_4$, $R_5$, $R_6$, $R_7$, $R_9$, $R_{10}$, $R_{11}$ and $R_{12}$ is independently selected from the group consisting of:

morpholine, piperidine, piperazine, imidazole and tetrazole;

m=0, 1, 2;

X=O or S and physiologically acceptable acids or salts thereof.

2. The method according to claim 1 wherein $Ar_2$ is naphthyl, tetrahydronaphthyl, indanyl or indenyl.

3. The method according to claim 2 wherein $Ar_2$ is naphthyl.

4. The method according to claim 3 wherein:

$Ar_2$ is 1-naphthyl;

L is $C_{1-6}$saturated or unsaturated branched or unbranched carbon chain wherein one or more methylene groups are optionally independently replaced by O,N or S; and wherein said linking group is optionally substituted with 0–2 oxo groups and one or more $C_{1-4}$ branched or unbranched alkyl which may be substituted by one or more halogen atoms;

$R_1$ is selected from the group consisting of $C_{3-10}$ alkyl branched or unbranched, cyclopropyl and cyclohexyl which may optionally be partially or fully halogenated and which may optionally be substituted with one to three $C_{1-3}$alkyl groups;

$R_3$ is selected from the group consisting of $C_{1-4}$alkyl branched or unbranched, cyclopropyl, phenyl, pyridinyl each being optionally substituted as described in claim 1, alkoxycarbonylalkyl, $C_{1-6}$alkyl branched or unbranched, cyclopropyl and cyclopentyl optionally substituted as described in claim 1.

5. The method according to claim 1 wherein the compound is chosen from:

1-[5-tert-Butyl-2-p-tolyl-2H-pyrazol-3-yl]-3-[4-(2-morpholin-4-yl-ethoxy)naphthalene-1-yl]-urea;

1-[5-tert-Butyl-2-p-tolyl-2H-pyrazol-3-yl]-3-[4-(2-(cis-2,6-dimethylmorpholin-4-yl)ethoxy)naphthalen-1-yl]-urea;

1-[5-tert-Butyl-2-p-tolyl-2H-pyrazol-3-yl]-3-[4-(2-(trans-2,6-dimethylmorpholin-4-yl)ethoxy)naphthalen-1-yl]-urea;

1-[5-tert-Butyl-2-p-tolyl-2H-pyrazol-3-yl]-3-[4-(2-(2-(methoxymethyl)morpholin-4-yl)ethoxy)naphthalen-1-yl]-urea;

1-[5-tert-Butyl-2-p-tolyl-2H-pyrazol-3-yl]-3-[4-(2-(morpholin-4-yl)-2-oxoethoxy)naphthalene-1-yl]-urea;

1-[5-tert-Butyl-2-p-tolyl-2H-pyrazol-3-yl]-3-[4-(2-(morpholin-4-yl)-2-methylethoxy)naphthalen-1-yl]-urea;

1-[5-tert-Butyl-2-p-tolyl-2H-pyrazol-3-yl]-3-[4-(2-(morpholin-4-yl)-1-methylethoxy)naphthalen-1-yl]-urea;

1-[5-tert-Butyl-2-p-tolyl-2-pyrazol-3-yl]-3-[4-(2-thiomorpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalene-1-yl]-urea;

1-[5-tert-Butyl-2-p-tolyl-2H-pyrazol-3-yl]-3-[4-(2-morpholin-4-yl-ethoxy)-3-methylnaphthalen-1-yl]-urea.

1-[5-tert-Butyl-2-p-tolyl-2H-pyrazol-3-yl]-3-[4-(2-(morpholin-4-yl-carbonyloxo)ethoxy)naphthalen-1-yl]-urea;

1-[5-tert-Butyl-2-p-tolyl-2H-pyrazol-3-yl]-3-[4-(3-morpholin-4-yl-propyl)naphthalene-1-yl]-urea;

1-[5-tert-Butyl-2-p-tolyl-2H-pyrazol-3-yl]-3-[4-(morpholin-4-yl-methyl)naphthanlen-1-yl]-urea;

1-[5-tert-Butyl-2-p-tolyl-2H-pyrazol-3-yl]-3-[4-(2-pyridin-4-yl-ethyl)naphthalen-1-yl]-urea;

1-[5-tert-Butyl-2-p-tolyl-2H-pyrazol-3-yl]-3-[4-(3-(morpholin-4-yl)propyn-1-yl)naphthanlen-1-yl]-urea;

1-[5-tert-Butyl-2-p-tolyl-2H-pyrazol-3-yl]-3-[4-(3-(piperdin-1-yl)propyn-1-yl)naphthalen-1-yl)-urea;

1-[5-tert-Butyl-2-p-tolyl-2H-pyrazol-3-yl]-3-[4-(3-(2-methoxymethylmorpholin-4-yl)propyl-1-yl)naphthalen-1-yl]-urea;

1-[5-tert-Butyl-2-p-tolyl-2H-pyrazol-3-yl]-3-[4-(pyridin-4-yl-methoxy)naphthalen-1-yl]-urea;

1-[5-tert-Butyl-2-p-tolyl-2H-pyrazol-3-yl]-3-yl-3-[4-(2-pyridin-4-yl-ethoxy)naphthalen-1-yl]-urea;

1-[5-tert-Butyl-2-p-tolyl-2H-pyrazol-3-yl]-3-[4-(3-pyridin-4-yl-propoxy)naphthalen-1-yl]-urea;

1-[5-tert-Butyl-2-p-tolyl-2H-pyrazol-3-yl]-3-[4-(2-imidazol-1-yl-ethoxy)naphthalen-1-yl]-urea;

1-[5-tert-Butyl-2-p-tolyl-2H-pyrazol-3-yl]-3-[4-(pyridin-4-yl-methylamino)naphthalen-1-yl]-urea;

1-[5-iso-Propyl-2-phenyl-2H-pyrazol-3-yl]-3-[4-(2-morpholin-4-yl-ethoxy)naphthalen-1-yl]-urea;

1-[5-cyclohexyl-2-phenyl-2H-pyrazol-3-yl]-3-[4-(2-morpholin-4-yl-ethoxy)naphthalen-1-yl]-urea;

1-[5-(2,2,2-trifluoroethyl)-2-phenyl-2H-pyrazol-3-yl]-3-[4-(2-morpholin-4-yl-ethoxy)naphthalen-1-yl]-urea;

1-[5-(1-methylcycloprop-1-yl)-2-phenyl-2H-pyrazol-3-yl]-3-[4-(2-morpholin-4-yl-ethoxy)naphthalene-1-yl]-urea;

1-[5-(1-methylcyclohex-1-yl)-2-phenyl-2H-pyrazol-3-yl]-3-[4-(2-morpholin-4-yl-ethoxy)naphthalen-1-yl]-urea;

1-[5-tert-butyl-2-methyl-2H-pyrazol-3-yl]-3-[4-(2-morpholin-4-yl-ethoxy)naphthalene-1-yl]-urea;

1-[5-tert-butyl-2-(4-chlorophenyl)-2H-pyrazol-3-yl]-3-[4-(2-morpholin-4-yl-ethoxy)naphthalen-1-yl]-urea;

1-[5-tert-butyl-2-butyl-2H-pyrazol-3-yl]-3-[4-(2-morpholin-4-yl-ethoxy)naphthalen-1-yl]-urea;

1-[5-tert-butyl-2-(4-methyl-3-carbamylphenyl)-2H-pyrazol-3-yl]-3-[4-(2-morpholin-4-yl-ethoxy)naphthalen-1-yl]-urea;

1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;

1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;

1-[5-tert-butyl-2-(3-dimethylaminomethylphenyl)-2H-pyrazol-3-yl]-3-[4-(2-morpholin-4-yl-ethoxy)naphthalen-1-yl]-urea;

1-[5-tert-butyl-2-(2-chloropyridin-5-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-morpholin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea;

1-[5-tert-butyl-2-(pyridin-3-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;

1-[5-tert-butyl-2-(2-methylpyridin-5-yl)-2H-pyrazol-3-yl]-3-[4-(3-morpholin-4-yl-propyn-1-yl)naphthalen-1-yl]-urea; and and the physiologically acceptable acids or salts thereof.

6. The method according to claim 5 wherein the compound is:

1-[5-tert-Butyl-2-p-tolyl-2H-pyrazol-3-yl]-3-[4-(2-morpholin-4-yl-ethoxy)naphthalen-1-yl]-urea.

* * * * *

UNITED STATES PATENT AND TRADEMARK OFFICE
CERTIFICATE OF CORRECTION

PATENT NO. : 6,333,325 B1  Page 1 of 1
DATED : December 25, 2001
INVENTOR(S) : Pier F. Cirillo, Thomas A. Gilmore, Eugene R. Hickey, John R. Regan and Lin-Hua Zhang It is certified that error appears in the above-identified patent and that said Letters Patent is hereby corrected as shown below:

<u>Column 64,</u>
Line 1, "$R_5$" should read -- $R_3$ --

Signed and Sealed this

Thirtieth Day of July, 2002

*Attest:*

*Attesting Officer*

JAMES E. ROGAN
*Director of the United States Patent and Trademark Office*